United States Patent [19]

Whitfill et al.

[11] Patent Number: 5,397,569

[45] Date of Patent: Mar. 14, 1995

[54] METHOD OF TREATING INFECTIOUS BURSAL DISEASE VIRUS INFECTIONS

[76] Inventors: Craig E. Whitfill, 1300 Wellstone Cir., Apex, N.C. 27502; John A. Thomas, 1206 Crestwood Dr., Fayetteville, Ark. 72701; Tommy L. Fredericksen, 591 Westford Rd., Ashford, Conn. 06278; Julius K. Tyczkowski, 111 Woodruff Ct., Cary, N.C. 27511; J. Paul Thaxton, Jr., 117 Campfire Cir., Brandon, Miss. 39240

[21] Appl. No.: 8,394

[22] Filed: Jan. 25, 1993

Related U.S. Application Data

[63] Continuation of Ser. No. 586,859, Sep. 21, 1990, which is a continuation-in-part of Ser. No. 480,678, Feb. 15, 1990, abandoned, which is a continuation-in-part of Ser. No. 416,035, Oct. 2, 1989, abandoned.

[51] Int. Cl.$^6$ .................. A61K 39/12; A61K 39/395; C07K 15/28
[52] U.S. Cl. .................. 424/178.1; 530/388.3; 530/389.4; 435/948; 424/233.1; 424/215.1; 424/204.1
[58] Field of Search .................. 424/89, 215.1, 233.1, 424/178.1; 530/387.1, 388.3, 389.4; 435/235.1, 948

[56] References Cited

U.S. PATENT DOCUMENTS

| | | | |
|---|---|---|---|
| 3,326,767 | 6/1967 | Holper et al. | 167/78 |
| 3,651,213 | 3/1972 | Wallis et al. | 424/89 |
| 3,846,543 | 11/1974 | Fields et al. | 424/89 |
| 3,853,467 | 12/1974 | Giaever | 435/5 |
| 4,092,116 | 5/1978 | Giaever | 435/5 |
| 4,458,630 | 7/1984 | Sharma et al. | 119/6.8 |
| 4,493,825 | 1/1985 | Platt et al. | 424/89 |
| 4,530,831 | 7/1985 | Lütticken et al. | 424/89 |
| 4,645,665 | 2/1987 | Apontoweil et al. | 424/89 |
| 4,659,569 | 4/1987 | Mitsuhashi et al. | 424/89 |
| 4,761,282 | 8/1988 | Apontoweil et al. | 424/89 |
| 4,824,668 | 4/1989 | Melchior, Jr. et al. | 424/89 |
| 4,867,975 | 9/1989 | Gelb, Jr. | 424/89 |
| 4,956,452 | 9/1990 | Snyder et al. | 424/86 |
| 5,057,314 | 10/1991 | Whitfill et al. | 424/89 |

FOREIGN PATENT DOCUMENTS

1041214 3/1957 Germany.

OTHER PUBLICATIONS

Box et al, J. Comp. Path. 79:475–506, 1969.
Fahey et al, *J. Gen. Virol.* vol. 70, pp. 1473–1481, 1989.
Stone et al, *PSEB Med*, vol. 128, pp. 525–530, 1968.
Higgins, *Avian Diseases*, vol. 14, pp. 579–586, 1970.
Wetz et al, *Archive Virology*, vol. 91, pp. 207–220, 1986.
Giambrone et al Poultry Science 65: 1287–1290, 1986.
Abdu, P. A. et al., "Infectious Bursal Disease," *Worlds Poultry Science* 42, 219 (1986).
Chambers, P. et al., "Location of a Neutralizing Epitope For The Haemagglutinin-Neuraminidase Glycoprotein Of Newcastle Disease Virus," *J. Gen. Virol.* 69, 2115 (1988).
Chettle, N. et al., "Comparison Of Virus Neutralizing And Precipitating Antibodies To Infectious Bursal Disease Virus And Their Effect On Susceptibility To Challenge," *Br. Vet. F.* 141, 146 (1985).
Fahey, K. et al., "A Conformational Immunogen on VP-2 of Infectious Bursal Disease Virus that Induces (List continued on next page.)

*Primary Examiner*—Christine M. Nucker
*Assistant Examiner*—Julie Krsek-Staples
*Attorney, Agent, or Firm*—Bell, Seltzer, Park & Gibson

[57] ABSTRACT

A method of producing active immunity against a viral disease in an animal subject comprises administering to the subject a vaccine complex consisting essentially of a live virus and a neutralizing factor bound to the live virus. The neutralizing factor is selected from the group consisting of antibodies and antibody fragments. The live virus is one capable of producing disease in the subject, and the antibody or antibody fragment is one capable of neutralizing the live virus. Preferred subjects are birds, a preferred virus is Infectious Bursal Disease Virus, and a preferred route of administration to birds is by in ovo administration.

49 Claims, 5 Drawing Sheets

OTHER PUBLICATIONS

Virus–Neutralizing Antibodies that Passively Protect Chickens," *J. Gen. Virol.* 70, 1473 (1989).

Gyles, N. and Whitfill, C., *Annual Report of Project Contributions to NE-60* (Oct. 1987).

Gyles, N. and Whitfill, C., *Annual Report of Project Contributions to NE-60* (Oct. 1986).

Higgins, D., "Interaction of Lentogenic Newcastle Disease Virus and Specific Antibodies within the Yolk Sac," *Avian Diseases* 14, 579 (1970).

Higgins, D., "Vaccination Response of Parentially Immune Chicks after Yolk-Sac Inoculation of the Embryo with Inactivated Newcastle Disease Virus," *Avian Diseases*, 98 (1970).

Meulemans, G. et al., "Protective Effects Of HN And F Glycoprotein-Specific Monoclonal Antibodies On Experimental Newcastle Disease," *Avian Pathology* 15, 761 (1986).

Mitsui, T. et al., "Combined Hepatitis B Immune Globulin And Vaccine For Postexposure Prophylaxis Of Accidental Hepatitis B Virus Infection In Hemodialysis Staff Members: Comparison With Immune Globulin Without Vaccine In Historical Controls," *Hepatology* 10, No. 3, 324 (1989).

Morrison, S. and Terres, G., "Enhanced Immunological Sensitization of Mice by the Simultaneous Injection of Antigen and Specific Antiserum (Part II)," *The Journal of Immunology* 96, No. 5, 901 (1966).

Naqi, S. et al., "Maternal Antibody And Its Effect On Infectious Bursal Disease Immunization," *Avian Diseases* 27, No. 3, 623 (1982).

Philipps, Luis Augusto et al., "Trials on passive immunization and treatment of Newcastle disease by use of plasma and Vitelo Hiperinmunes," *La Vida Agricola*, Feb. 1956, pp. 111–120.

Randall, R., "Solid Matrix–Antibody–Antigen (SMAA) Complexes for Constructing Multivalent Subunit Vaccines," *Immunology Today* 10, No. 10, 336 (1989).

Randall, R., and Young, D., "Immunization Against Multiple Viruses by Using Solid–Matrix–Antibody–Antigen Complexes," *Journal of Virology* 63, No. 4, 1808 (1989).

Randall, R. and Young, D., "Humoral and Cytotoxic T Cell Immune Responses to Internal and External Structure Proteins of Simian Virus 5 Induced by Immunization with Solid Matrix–Antibody–Antigen Complexes," *J. Gen. Virol.* 69, 2505 (1988).

Sharma, Padma N. et al., "Role of Maternal Antibodies in Immunization of Chicks Against Newcastle Disease Virus," *Zootecnica International* (Jun. 1989).

Stone, H. and Boney, W., "Vaccination of Congenitally-Immune Chicks against Newcastle Disease Virus (33057)," *PSEB Med.* 128, 525 (1968).

Terres, G. and Wolins, W., "Enhanced Sensitization in Mice by Simultaneous Injection of Antigen and Specific Rabbit Antiserum," 632.

Terres, G. and Wolins, W., "Enhanced Immunological Sensitization Of Mice By The Simultaneous Injection Of Antigen And Specific Antiserum. I. Effect Of Varying The Amount Of Antigen Used Relative To The Antiserum," 86, 361.

Vasington, J. et al., "Studies on the Protective Value of Newcastle–Immune Serum and Gamma Globulin Against Artifically Induced Newcastle Disease of Chickens," *Poultry Science* 39, 1418 (1960).

Vasington, Paul J., "Studies on the Serological Response to and Protective Value of Immune Serum and Gamma Globulin in Chickens Artificially Inoculated with Newcastle Disease Virus," Masters Thesis, University of Maryland, 1959.

Wetz, K. et al., "Neutralization Of Poliovirus By Polyclonal Antibodies Requires Binding Of A Single IgG Molecule Per Virion," *Archives of Virology* 91, 207 (1986).

The Merck Manual, 2nd Ed., 311 (1981).

Hagan and Bruner 7th Ed., 673 (1981).

Simonyi et al., *Acta Veterinari Academice Scientiarum Hungaricae* 3, 237–243 (1968).

Regressor Sera
↓
100 K Spectrum Hollow Fiber

≤100 K fraction
(Very little
Anti-IBDV
activity)

>100 K fraction (5069)
(See Fig. 8)

TSK First Pass (5070) (moderately clean; See Fig. 9)

TSK Second Pass (5077) (clean; See Fig. 10)

TSK Third Pass (5079) (very clean; See Fig. 11)

FIG. 3.

Elution Profile of >50K Sera Component of Arkansas Regressor Sera

Elution Profile of Peak I of Fig. 4.

Elution Profile of Peak II of Fig. 4

Elution Profile of Peak III of Fig. 4

Elution Profile of >100K Sera Component of Arkansas Regressor Sera

Elution Profile of First Recycling of Peak II of Fig. 8

Elution Profile of Second Recycling of Peak II of Fig. 8

Elution Profile of Third Recycling of Peak II of Fig. 8

Elution Profile of Prior VNF Preparation

METHOD OF TREATING INFECTIOUS BURSAL DISEASE VIRUS INFECTIONS

RELATED APPLICATIONS

This application is a continuation of application Ser. No. 07/586,859, filed 21 September 1990, which is a continuation-in-part of co-pending Application Ser. No. 07/480,678, filed Feb. 15, 1990, and titled "Method of Treatment," now abandoned, which is a continuation-in-part of co-pending application Ser. No. 07/416,035, filed Oct. 2, 1989, and titled "PURIFICATION OF VIRAL NEUTRALIZING FACTOR, now abandoned."

FIELD OF THE INVENTION

The present invention relates to methods of producing active immunity by administering subjects a vaccine conjugate, which conjugate is comprised of a live virus and a neutralizing antibody or fragment thereof.

BACKGROUND OF THE INVENTION

Gyles et al., 47 *Poultry Sci.* 430 (1968), and Gyles and Brown, 50 *Poultry Sci.* 901 (1971), found that regression of Rous sarcoma virus (RSV)-induced tumors is under genetic control in Arkansas progressor line and Arkansas regressor line chickens. Whitfill et al., 61 *Poultry Sci.* 1573 (1982), reported a low molecular weight fraction that was isolated by gel permeation chromatography from Arkansas regressor chicken sera. The active low molecular weight fraction was called the low molecular weight viral neutralizing factor (VNF). See Whitfill et al., 17 *Immunogenetics* 387 (1983).

Gyles and Whitfill, *Annual Report of Project Contributions to NE-60* (Oct. 1986), subsequently reported that VNF neutralized Rous sarcoma virus and Newcastle's Disease virus when administered in combination therewith to nine day old SPAFAS egg embryos as measured by chorioallantoic membrane pock formation. Later, Gyles and Whitfill, *Annual Report of Project Contributions to NE-60* (Oct. 1987), reported that VNF neutralized Infectious Bursal Disease Virus (IBDV) and Infectious Bronchitis Virus (IBV) when administered in combination therewith to nine day old SPAFAS egg embryos, and had antimicrobial activity. It has not heretofore been suggested that VNF is a viral neutralizing antibody.

Viral neutralizing antibodies are antibodies which can neutralize the infectivity of a virus if the virus and antibodies are allowed to react together for a sufficient time. Such a procedure is carried out during the course of performing a neutralization test. The neutralization test, which was the first technique used to detect antibodies against virus in serum, can be done with virtually any virus. See generally *Handbook of Experimental Immunology*, 37.9 (D. M. Weir Ed. 2d ed. 1973)(Blackwell Scientific Publications).

N. Phillips, 33 *Vira. Agr. (Lima E. sum.)* 111 (1956)(Summarized in J. Vasington et al., 39 *Poultry Sci.* 1418, 1419 (1960)), in an attempt to confer immediate and lasting immunity against Newcastle Disease Virus in birds, studied the effect of plasma and yolk in combination with live virus. The plasma was obtained from birds that survived a natural outbreak of the disease and the yolk was obtained from eggs produced by the same birds. The results of these studies showed that all chickens receiving simultaneous inoculations of the plasma-yolk mixture and virus, and those which received the virus two days later, survived challenge with artificial inoculation.

J. Vasington et al., 39 *Poultry Sci.* 1418 (1960), investigated the protective value of Newcastle Disease Virus immune serum and gamma globulin against Newcastle Disease virus challenge in 4 to 5 week old chickens. Challenge was carried out simultaneous with or subsequent to administration of the immune serum or gamma globulin. Simultaneous administration of NDV and gamma globulin in one bird was found to protect the bird against death, but did not lead to active immunity. See Id. at 1424 Table 4 and accompanying text. It is not suggested that the virus and antibody be administered as a complex.

H. Stone and W. Boney, 128 *P.S.E.B. Med.* 525 (1968), report the vaccination of 1-2 day old chicks against Newcastle Disease Virus with a vaccine containing chemically inactivated virus antigen in the form of antigen-antibody complexes, free homologous antibody, and an aluminum hydroxide adjuvant. The complexing of the antigen with the inactivated virus did not lead to increased protection against challenge, see Id. at 528, and the data indicated that the use of an adjuvant was critical to the results.

D. Higgins, 14 *Avian Diseases* 579, 585 (1970), notes that the presence of maternal neutralizing antibodies in the yolk of eggs from hens immune to Newcastle's Disease Virus (NDV) is well known. Higgins suggests that, if the antibody-antigen complex formed after yolk sac inoculation of NDV diffuses throughout the embryonic tissues prior to hatching, as do uncombined yolk sac antibodies, and persists in the neonatal chick, it may later stimulate active anti-NDV immunity. Higgins does not suggest that neutralizing antibodies be complexed with a live virus to attenuate that virus, and the complex then administered as a vaccine.

Platt et al., U.S. Pat. No. 4,493,825, disclose a vaccine complex comprised of an immunizing agent with an antibody bound thereto, the antibody in turn having a microparticle bound thereto. Pathogenic microorganisms, whole virus, and antigenic proteins are suggested as immunizing agents. The authors state that the ability to use such complexes as vaccines is surprising, because the immunizing activity of the antigenic protein would have been thought to have been interfered with by the antibody binding. See Col. 2, lines 14-17 therein. The authors do not suggest that their vaccine would be operable without the inclusion of the microparticle, do not suggest that neutralizing antibodies be used, do not suggest that live virus capable of causing disease (i.e., pathogenic) be used, do not suggest that the conjugation of an antibody to a live virus will protect a subject against infection by that live virus, and do not suggest that a neutralizing antibody should be used to obtain protection against infection by a pathogenic live virus when a pathogenic live virus is used as the immunizing agent.

K. Fahey et al., 70 *J. Gen. Virol.* (1989), disclose a viral neutralizing antibody to IBDV. The antibody, which was monoclonal in origin, was used to separate a structural protein from solubilized viral particles for the purpose of developing a subunit vaccine for IBDV. It is not suggested that the viral neutralizing antibody would protect a subject against IBDV so that the IBDV, with the neutralizing antibody bound thereto, could be administered as a live vaccine.

SUMMARY OF THE INVENTION

The present invention is based on our ongoing efforts to characterize Viral Neutralizing Factor (VNF). During this research, the active component of prior preparations of VNF was unexpectedly found to be a higher molecular weight contaminant in these generally lower molecular weight preparations. Specifically, VNF was found to be a viral neutralizing antibody. This finding makes available new uses of viral neutralizing antibodies, and fragments thereof, in the production of live attenuated viral vaccines. In view of the tendency of maternal antibodies in chicks to interfere with the development of active immunity to a live virus challenge, see P. Abdu et al., *Worlds Poultry Science V* 42, 219, (1968); P. Sharma et al., *Zootecnica International,* 51 (June 1989), these results are particularly unexpected.

The present invertion accordingly provides a method of producing active immunity against a viral disease in an animal subject, the method comprising administering to the subject a vaccine conjugate comprised of a live virus and a neutralizing factor bound to the live virus. The neutralizing factor is selected from the group consisting of antibodies and antibody fragments. The antibody or antibody fragment is one capable of neutralizing the live virus. The vaccine conjugate is administered in an amount effective to produce an immune response to the live virus in the subject.

Another aspect of the present invention is a vaccine preparation useful for producing active immunity against a viral disease in an animal subject. The vaccine preparation is a pharmaceutically acceptable formulation which comprises a vaccine conjugate. The vaccine conjugate comprises a live virus and a neutralizing factor bound to the live virus. The neutralizing factor is selected from the group consisting of antibodies and antibody fragments. The antibody or antibody fragment is capable of neutralizing the live virus. The vaccine conjugate is included in the pharmaceutically acceptable formulation in an amount effective to produce an immune response to the live virus in the subject.

Another aspect of the present invention is an article of manufacture comprising a closed, pathogen-impermeable, container and a sterile vaccine formulation as described above enclosed within the container.

BRIEF DESCRIPTION OF THE DRAWINGS

FIGS. 1, 2, and 3 schematically illustrate the various preparations from Arkansas regressor line chicken sera that have been used for the purification of VNF and the determination of relative VNF activities.

DETAILED DESCRIPTION OF THE INVENTION

Figure 1:
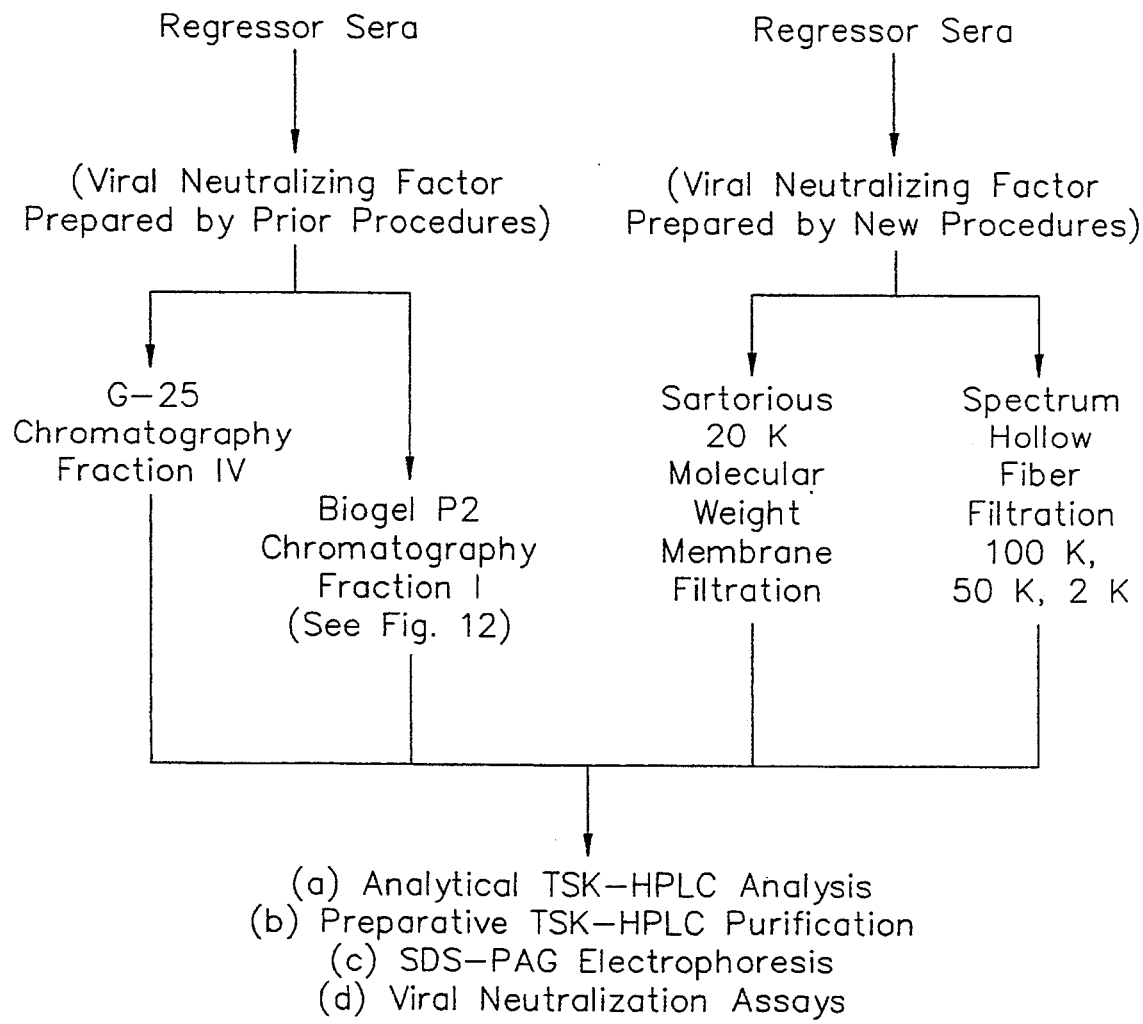

Antibodies used in practicing the present invention are viral neutralizing antibodies. Viral neutralizing antibodies are those which combat the infectivity of a virus in vitro if the virus and the antibodies are allowed to react together for a sufficient time. The source of the viral neutralizing antibody is not critical. They may originate from any animal, including birds (e.g., chicken, turkey) and mammals (e.g., rat, rabbit, goat, horse). The viral neutralizing antibodies may be polyclonal or monoclonal in origin. See, e.g., D. Yelton and M. Scharff, 68 *American Scientist* 510 (1980). The antibodies may be chimeric. See, e.g., M. Walker et al., 26 *Molecular Immunology* 403 (1989). The antibodies may be of the type heretofore known as Viral Neutralizing Factor (VNF). See, e.g., Gyles and Whitfill, supra. VNF used for practicing the present invention may be obtained from the Giant Jungle Fowl (Gallus gallus) and strains of birds derived from Gallus gallus which are capable of producing VNF. Exemplary of such derivative strains is the Arkansas regressor chicken line. Among other means, stocks of birds can be located through the *International Registry of Poultry Genetics Stocks, Bulletin No.* 476, Agriculture Publication No. U-351376 (available from the University of Connecticut, Storrs, Conn.).

Viral neutralizing antibodies used in practicing the present invention may be immunoglobulins of any isotype, including IgM, IgG, IgA, IgD, and IgE immunoglobulins. IgG and IgM are more preferred, and IgG immunoglobulins (e.g., IgG1, IgG2, IgG3, IgG4) are most preferred.

Antibody fragments used in practicing the present invention are fragments of viral neutralizing antibodies which retain the variable region binding site thereof. Exemplary are F(ab')$_2$ fragments, F(ab') fragments, and Fab fragments. See generally Immunology: Basic Processes, 95–97 (J. Bellanti Ed. 2d ed. 1985).

Antibodies or antibody fragments used in practicing the present invention may have additional elements joined thereto. For example, a microsphere or microparticle may be joined to the antibody or antibody fragment, as described in U.S. Pat. No. 4,493,825 to Platt, the disclosure of which is incorporated herein by reference.

The present invention is particularly advantageously employed with viruses which would be pathogenic (i.e., capable of causing disease) in the subject being treated if not for their conjugation to the neutralizing factor. The pathogenicity of the virus may be inherent in the virus itself (e.g., a virus such as Infectious Bursal Disease Virus which is difficult to attenuate) or due to the susceptibility of the subject to be treated (e.g., birds in ovo). In general, many pathogenic viruses have the positive effect of evoking active immunity in subjects infected therewith, and many attenuated vaccine strains of virus have the capability of causing at least some disease in subjects. Hence, the term "pathogenic," as used to describe viruses herein, means that the harm caused to subjects by administration of the virus outweighs any benefit which would result therefrom. It is preferred that the virus be one capable of producing an active immune response thereto in the subject being treated.

The vaccine conjugate is included in the vaccine formulations in an amount per unit dose sufficient to evoke an active immune response to the virus in the subject to be treated. The term "immune response," as used herein, means any level of protection from subsequent exposure to the virus which is of some benefit in a population of subjects, whether in the form of decreased mortality, decreased lesion scores, improved feed conversion ratios, or the reduction of any other detrimental effect of the disease, regardless of whether the protection is partial or complete.

With respect to the degree of protection provided by the neutralizing factor, the quantity of the neutralizing factor administered in combination with the virus in the vaccine need not be sufficient to provide complete protection from the virus, as long as the detrimental response produced by the virus is reduced to a level at which the benefits of the immune response produced outweigh any harm resulting from the infection. Preferably, with respect to avian subjects administered VNF, birds are administered between about 10 and about 1,000 Activity Units per dose of vaccine conjugate. Pharmaceutical compositions are compounded to include these quantities of VNF per unit dose.

Viruses which may be mixed with the neutralizing factor to form a vaccine include both mammalian and avian viruses. Exemplary of mammalian viruses are the Japanese Encephalitis Virus, Influenza Virus, Sendai Virus, Measles Virus, Human Influenza Virus and Pseudorabies. See, e.g., U.S. Pat. Nos. 4,659,569 and 4,493,825. Exemplary of avian viruses are Rous Sarcoma Virus, Newcastle's Disease Virus, Infectious Bursal Disease Virus, and Infectious Bronchitis Virus.

The term "Infectious Bursal Disease Virus" (IBDV), as used herein, encompasses all strains of IBDV. Exemplary are the Bursal Disease Vaccine, Lukert strain, live virus, which is obtained from either Vineland Laboratories in Vineland, New Jersey or Salsbury Laboratories in Charles City, Iowa, the Bursal disease virulent challenge virus, which is obtained from the U.S.D.A. in Ames, Iowa (original isolate from S. A. Edgar), and Infectious Bursal Disease Virus strain VR2161, disclosed in U.S. Pat. No. 4,824,668 to Melchior and Melson.

The term "Rous Sarcoma Virus" (RSV), as used herein, encompasses all strains of RSV. RSV has been comprehensively studied since its discovery early this century. See generally 1 RNA Tumor Viruses: Molecular Biology of Tumor Viruses, Second Edition, 59–61 (R. Weiss, N. Teich, H. Varmus and J. Coffin eds. 1984). An assay technique for Rous Sarcoma Virus is reported at Brit. J. Exptl. Med., 99:183. Moloney, J. Nat. Cancer Inst., 16:877, reports the development of standard lots of the virus for use in quantitative investigations. See also U.S. Pat. No. 3,326,767 to Holper and Kiggins. Numerous Rous sarcoma virus strains are listed in the ATCC Catalogue of Animal and Plant Viruses, Chlamydiae, Rickettsiae and Virus Antisera (5th ed. 1986), at pages 110–112.

The term "Infectious Bronchitis Virus" (IBV), as used herein, encompasses all strains of IBV. Exemplary are Mass. 41 Strain, Arkansas 99 Strain, Conn. A5968, and Michigan State University Repository Code 42 Strain, all available from American Type Culture Collection, Rockville, Md. The term "Newcastle's Disease Virus" encompasses all strains of Newcastle's Disease Virus.

The term "animals," as used herein, is intended to include, among other things, both mammals and birds. Exemplary mammals include mice, rats, guinea pigs, rabbits, ferrets, dogs, cats, cows, horses and primates including man. The term "bird" is intended to include males or females of any avian species, but is primarily intended to encompass poultry which are commercially raised for eggs or meat. Accordingly, the term "bird" is particularly intended to encompass hens, cocks and drakes of chickens, turkeys, ducks, geese, quail and pheasant. Domestic animals (i.e., non-human animals), are preferred.

Animals may be administered vaccines of the present invention by any suitable means. Exemplary are by oral administration, by intramuscular injection, by subcutaneous injection, by intravenous injection, by intraperitoneal injection, by eye drop or by nasal spray. When the animal to be treated is a bird, the bird may be a hatched bird, including a newly hatched (i.e., about the first three days after hatch), adolescent, and adult birds. Birds may be administered the vaccine in ovo, as described in U.S. Pat. No. 4,458,630 to Sharma (the disclosure of this and all other patent references cited herein is to be incorporated herein by reference).

The in ovo administration of the vaccine involves the administration of the vaccine to eggs. Eggs administered the vaccine of the present invention are fertile eggs which are preferably in the fourth quarter of incubation. Chicken eggs are treated on about the fifteenth to nineteenth day of incubation, and are most preferably treated on about the eighteenth day of incubation (the eighteenth day of embryonic development). Turkey eggs are preferably treated on about the twenty-first to twenty-sixth day of incubation, and are most preferably treated on about the twenty-fifth day of incubation.

Eggs may be administered the vaccine of the invention by any means which transports the compound through the shell. The preferred method of administration is, however, by injection. The site of injection is preferably within either the region defined by the amnion, including the amniotic fluid and the embryo itself, in the yolk sac, or in the air cell. Most preferably, injection is made into the region defined by the amnion. By the beginning of the fourth quarter of incubation, the amnion is sufficiently enlarged that penetration thereof is assured nearly all of the time when the injection is made from the center of the large end of the egg along the longitudinal axis.

The mechanism of egg injection is not critical, but it is preferred that the method not unduly damage the tissues and organs of the embryo or the extraembryonic membranes surrounding it so that the treatment will not decrease hatch rate. A hypodermic syringe fitted with a needle of about 18 to 22 gauge is suitable for the purpose. To inject into the air cell, the needle need only be inserted into the egg by about two millimeters. A one inch needle, when fully inserted from the center of the large end of the egg, will penetrate the shell, the outer and inner shell membranes enclosing the air cell, and the amnion. Depending on the precise stage of development and position of the embryo, a needle of this length will terminate either in the fluid above the chick or in the chick itself. A pilot hole may be punched or drilled through the shell prior to insertion of the needle to prevent damaging or dulling of the needle. If desired, the egg can be sealed with a substantially bacteriaimpermeable sealing material such as wax or the like to prevent subsequent entry of undesirable bacteria.

It is envisioned that a high speed automated egg injection system for avian embryos will be particularly suitable for practicing the present invention. Numerous such devices are available, exemplary being those disclosed in U.S. Pat. No. 4,681,063 to Hebrank and U.S. Pat. Nos. 4,040,388, 4,469,047, and 4,593,646 to Miller. All such devices, as adapted for practicing the present invention, comprise an injector containing the vaccine described herein, with the injector positioned to inject an egg carried by the apparatus with the vaccine. Other features of the apparatus are discussed above. In addition, if desired, a sealing apparatus operatively associated with the injection apparatus may be provided for sealing the hole in the egg after injection thereof.

Preferred egg injection apparatus for practicing the present invention is disclosed in U.S. Pat. Nos. 4,681,063 and 4,903,635 to Hebrank, the disclosures of which are incorporated herein by reference. This device comprises an injection apparatus for delivering fluid substances into a plurality of eggs and suction apparatus which simultaneously engages and lifts a plurality of individual eggs from their upwardly facing portions and cooperates with the injection means for injecting the eggs while the eggs are engaged by the suction apparatus. The features of this apparatus may be combined with the features of the apparatus described above for practicing the present invention. Preferred subjects for carrying out the present invention are birds.

The method of the present invention is preferably carried out on birds in ovo. A preferred virus for use in carrying out the present invention is Infectious Bursal Disease Virus.

A vaccine conjugate of the present invention is made by mixing the neutralizing factor with a live virus in a pharmaceutically acceptable carrier for a time sufficient to form a live virus-neutralizing factor conjugate (for example, by combining the neutralizing factor and virus in a common liquid carrier for at least about one hour prior to administration to a subject). This can advantageously be carried out by simply adding hyperimmune sera containing VNF to an aqueous solution containing the live virus. Vaccine formulations of the present invention preferably comprise the vaccine conjugate in lyophilized form or the vaccine conjugate in a pharmaceutically acceptable carrier. Pharmaceutically acceptable carriers are preferably liquid, particularly aqueous, carriers. For the purpose of preparing such vaccine formulations, the neutralizing factor and virus may be mixed in sodium phosphate-buffered saline (pH 7.4) or conventional media such as MEM. The vaccine formulation may be stored in a sterile glass container sealed with a rubber stopper through which liquids may be injected and formulation withdrawn by syringe.

Vaccine formulations of the present invention may optionally contain one or more adjuvants. Any suitable adjuvant can be used, including chemical and polypeptide immunostimulants which enhance the immune system's response to antigens. Preferably, adjuvants such as aluminum hydroxide, aluminum phosphate, plant and animal oils, and the like are administered with the vaccine conjugate in an amount sufficient to enhance the immune response of the subject to the vaccine conjugate. The amount of adjuvant added to the vaccine conjugate will vary depending on the nature of the adjuvant, generally ranging from about 0.1 to about 100 times the weight of the virus, preferably from about 1 to about 10 times the weight of the virus.

The vaccine formulations of the present invention may optionally contain one or more stabilizer. Any suitable stabilizer can be used, including carbohydrates such as sorbitol, manitol, starch, sucrose, dextrin, or glucose; proteins such as albumin or casein; and buffers such as alkaline metal phosphate and the like. The use of a stabilizer is particularly advantageous when the vaccine formulation is a lyophilized formulation.

A preferred embodiment of the present invention provides a method of producing active immunity against Infectious Bursal Disease Virus in an avian subject by administering to the subject, at a time ranging between about the last quarter of in ovo incubation and about the first three days after hatch, a vaccine conjugate comprising live infectious bursal disease virus and a neutralizing factor bound to the live virus. The neutralizing factor is preferably selected from the group consisting of IgG immunoglobulins and IgG immunoglobulin fragments, and is capable of neutralizing the live virus. The vaccine conjugate is administered in an amount effective to produce active immunity against infectious bursal disease virus in said subject. In a specific example, hyperimmune serum from chickens prepared against infectious bursal disease virus is mixed in the proportions described in the following Examples to form a conjugate (e.g., 22 $EID_{50}$s of virus with 136 Units per 50 $\mu L$ hyperimmune serum; 2.2 $EID_{50}$s of virus with 338 Units per $\mu L$ hyperimmune serum). The virus is IBD-BLEN ™ infectious bursal disease virus vaccine available from Sanofi Animal Health, Berlin, Md., USA, Tel. (301) 641-2060. The conjugate is then lyophylized to dryness as a final vaccine product in a vial and stored. For use, the vaccine conjugate is redissolved in diluent and 100 microliters per dose is injected subcutaneously into the neck of the chicken at during normal post-hatch processing (usually day 1 or 2 after hatch).

Another exemplary embodiment of the present invention provides a method of producing active immunity against Newcastle's Disease Virus in an avian subject by administering to the subject, at a time ranging between about the last quarter of in ovo incubation and about the first three days after hatch, a vaccine conjugate comprising live Newcastle's disease virus and a neutralizing factor bound to the live virus. The neutralizing factor is preferably selected from the group consisting of IgG immunoglobulins and IgG immunoglobulin fragments, and is capable of neutralizing the live virus. The vaccine conjugate is administered in an amount effective to produce active immunity against Newcastle's disease virus in the subject.

The present invention is described in greater detail in the following Examples. These examples are provided for illustrative purposes only, and are not to be taken as limiting.

EXAMPLE 1

Experimental Animals

The birds used for challenge with Rous sarcoma virus and subsequent sera collection were of the Arkansas regressor chicken line and the Arkansas progressor chicken line described in Gyles et al., 46 *Poultry Sci.* 465 (1967), flocks of which are maintained at the Agricultural Research Farm of the University of Arkansas, Fayetteville, Ark., 72701.

EXAMPLE 2

Standard Inoculum of Rous Sarcoma Virus

A standard inoculum of RSV-RAV-1 to be used to stimulate the production of antiviral factor in regressor chicken sera was prepared with an RSV-RAV-1 Bryan High Titer Strain identified as Lot #1 prepared for American Type Culture Collection in Rockville, Md. by Dr. John P. Bader, NCI, NIH. The titer was $2 \times 10^6$ PFU per milliliter and was stored at $-70°$ C. before use. Inoculation of birds was accomplished by infecting a standard inoculum of 0.1 milliliter of diluted RSV-RAV-1 into the left wing web as described in Whitfill et al., 61 *Poultry Sci.* 1573 (1981).

COMPARATIVE EXAMPLE A

Preparation of Regressor Chicken Hyperimmune Sera

The object of this example is to demonstrate for comparative purposes prior procedures for preparing tumor homogenate from susceptible chickens to be used to boost regressor chickens to induce production of viral neutralizing factor from hyperimmune sera. Regressor chickens were challenged with a standard inoculum of RSV, and after complete tumor regression as measured by visible disappearance of tumors, were injected once weekly for at least three weeks with a standard inoculum of Rous sarcoma tumor homogenate (RSTH) booster. Five days after the last booster RSTH injection, 20 milliliters of blood was removed from each chicken by cardiac puncture and allowed to clot for one hour at room temperature. Clotted blood was sedimented at 3000 $\times$g at room temperature in a Sorvall centrifuge for ten minutes and hyperimmune sera was removed and stored at 5 degrees Celsius. This routine was continued for several weeks on a given group of donor regressor chickens.

COMPARATIVE EXAMPLE B

Preliminary Purification of Low Molecular Weight Antiviral Factor (LMF)

The object of this example is to demonstrate for comparative purposes prior techniques for partially purifying viral neutralizing factor from a large volume of hyperimmune regressor chicken sera. Approximately 400 milliliters of regressor chicken hyperimmune sera prepared according to Comparative Example A above was applied to a SEPHADEX G-25 TM fine column (8 $\times$35 centimeters) and eluted at 250 milliliters per hour with 0.005M sodium phosphate buffer, pH 7.0. Four peaks were eluted from the column and peak IV, the last to elute at 2800 milliliters, contained the VNF activity against RSV-RAV-1. Peak IV was shown to neutralize RSV-RAV-1 by incubation with the virus with subsequent injection into wing-webs of susceptible chickens, as previously described for SEPHADEX G-100 TM fraction II. See Whitfill et al., 61 *Poultry Sci.* 1573 (1981). Peak IV typically eluted in a total volume of 1000 milliliters of buffer at 28 milliliters per tube and was freeze dried and redissolved at a concentration of 100 milligrams per milliliter in sterile distilled water.

COMPARATIVE EXAMPLE C

Further Purification of SEPHADEX G-25 Peak IV Utilizing BIOGEL P-2 TM Column Chromatography The object of this Example is to demonstrate for comparative purposes prior techniques for the further purification and desalting of viral neutralizing factor from earlier preliminary active fractions utilizing gel filtration column chromatography.

Approximately 35 milliliters of redissolved SEPHADEX G-25 TM peak IV (3500 milligrams) obtained as described in Comparative Example B above was applied to a BIOGEL P-2 TM column (5 centimeters$\times$40 centimeters), and eluted in distilled water at a flow rate of 90 milliliters per hour. The antiviral activity was found against RSV-RAV-1 in the first peak (Peak I) eluting at the void volume after 390 milliliters at 14 milliliters per tube. This peak I, eluting in a total volume of 100 milliliters, was freeze dried to dryness and the salt free preparation represented the more highly purified preparation of VNF. Approximately 5–10 milligrams of further purified VNF typically resulted from peak I of the BIOGEL P-2 TM column. A stock solution of the VNF in phosphate-buffered saline or distilled water was freshly prepared to a concentration of 5 milligrams per milliliter before testing for activity.

One activity unit for this stock solution is defined as the amount of activity against Rous sarcoma virus in one milliliter of this VNF solution. One milliliter of this solution will completely neutralize 500 standard doses of Rous sarcoma virus. A standard dose of Rous sarcoma virus is defined as that dilution of virus in 100 microliters that will produce an average of 70 pocks on SPF nine day old embryo chorioallantoic membranes by day 16. VNF is not toxic to a preparation of $7 \times 10^4$ chicken fibroblasts until a dose level of 0.1 Activity Unit is reached.

EXAMPLE 3

Preparation of Delipidated Regressor Line Hyperimmune Sera

This example demonstrates the currently preferred technique for preparing regressor chicken Hyperimmune Sera. The sera was prepared as described in Comparative Example A above, except that clotted blood was centrifuged at 3000 rpm for 15 minutes to remove particulate matter, and the resulting sera then filtered through a 5 micron, 1.2 micron, and 0.45 micron filter respectively. Finally, the sera is passaged through C18 cartridges to remove the lipid contained in the sera.

EXAMPLE 4

Concentration and Hollow Fiber Filtration of Delipidated Hyperimmune Sera

Figure 2:
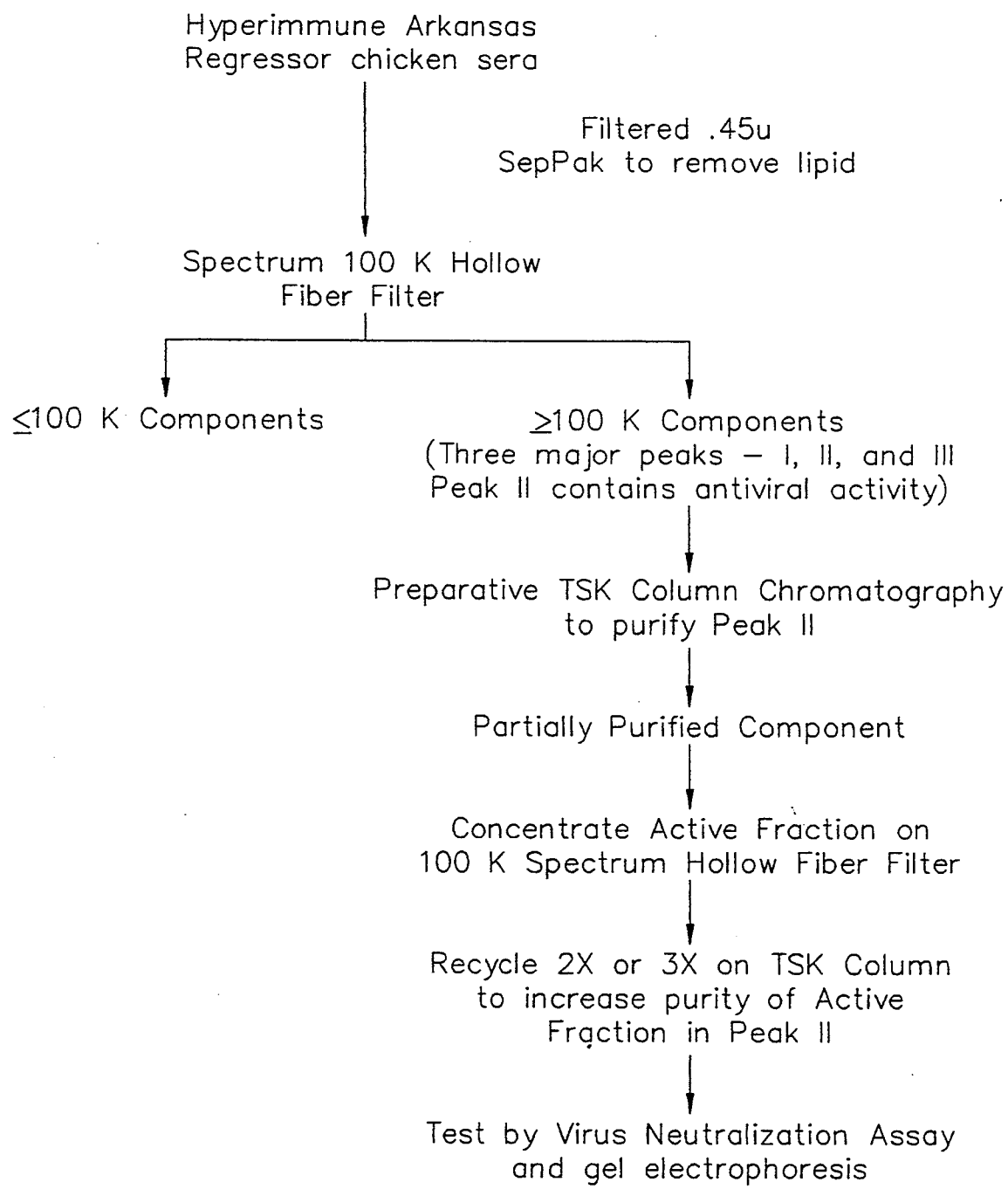

A schematic overview of the currently preferred procedure for purifying VNF is given in FIGS. 1, 2 and 3. This example gives additional information on the procedures described in these Figures.

A sera prepared as described in example 3 above is circulated through a SPECTRUM TM 50 k or 100 k hollow fiber breaker (available from Spectrum, Los Angeles, Calif., USA) and concentrated at least 4 fold for the greater than 50,000 molecular weight fraction ($\geq$50 k sera component) or the greater than 100,000 molecular weight fraction ($\geq$100 k sera component). Either the $\geq$50 k sera or the $\geq$100 k sera component is further fractionated on a preparative TSK column in accordance with the procedures described in Example 5 below, with the VNF being contained in the 150 k to 180 k portion of each sera component.

EXAMPLE 5

Separation of >50 k or >100 k Sera Components On a Preparative TSK ™ Column

Figure 4:
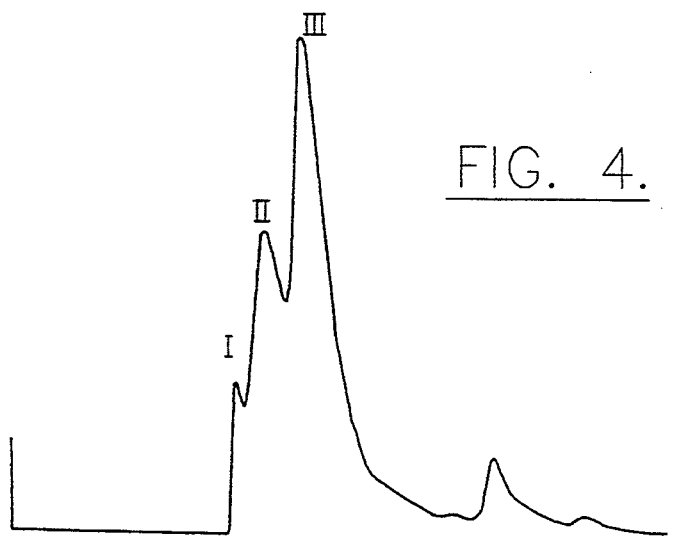
FIG. 4 illustrates the elution profile of the $\geq 50$ k sera component of Arkansas regressor line chicken sera by TSK ™ chromatography.
Figure 5:
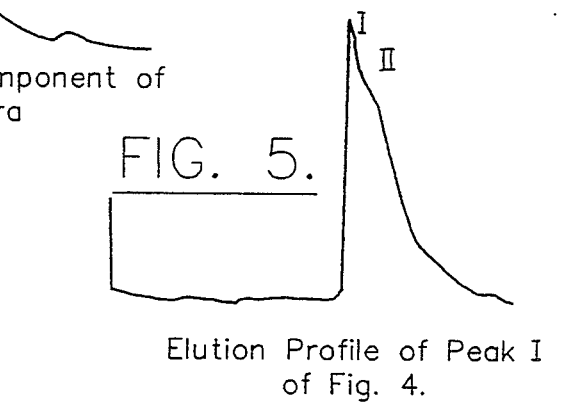
FIG. 5 illustrates, by TSK ™ chromatography, the elution profile of the peak I component shown in FIG. 4.
Figure 6:
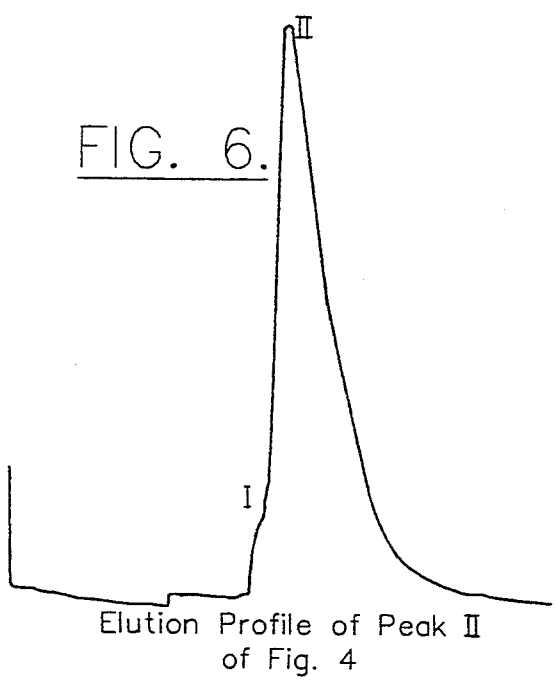
FIG. 6 illustrates the elution profile, by TSK ™ chromatography, of the peak II component shown in FIG. 4.
Figure 7:
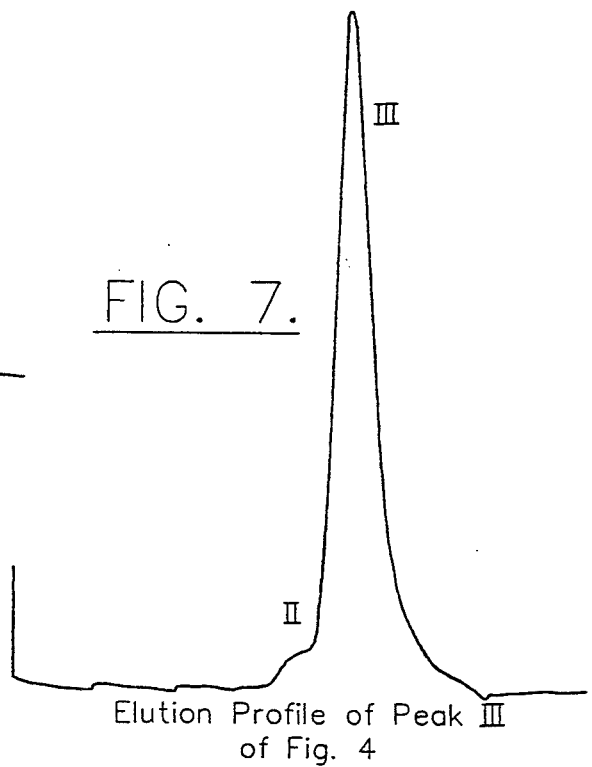
FIG. 7 illustrates the elution profile, by TSK ™ chromatography, of the peak III component shown in FIG. 4.
Figure 8:
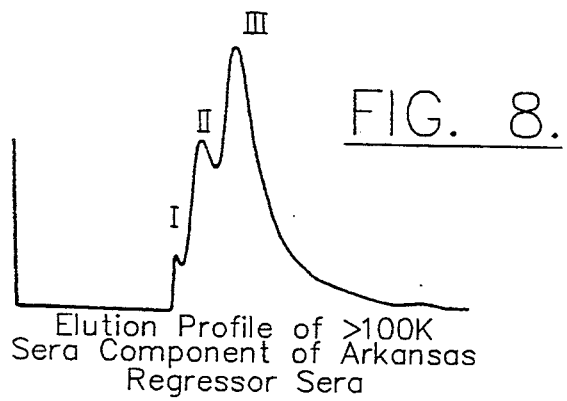
FIG. 8 illustrates the elution profile of the $\geq 100$ k sera component of Arkansas regressor line chicken sera by TSK ™ chromatography.
Figure 9:
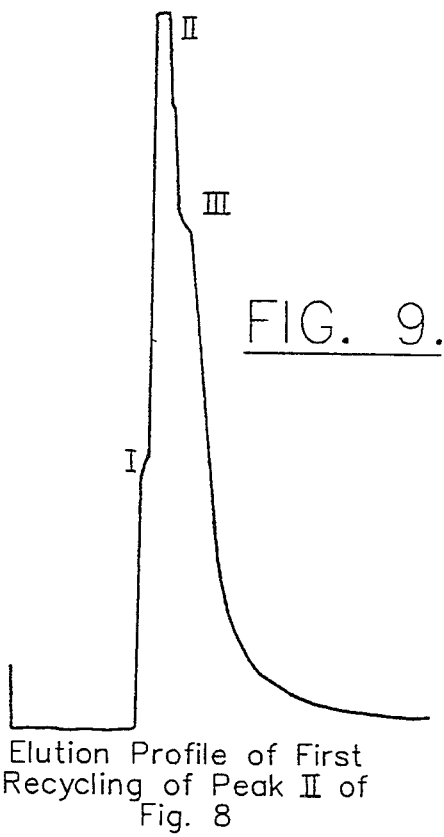
FIGS. 9 through 11 illustrate the increased purification of VNF achieved by first, second, and third recyclings of the peak II component illustrated in FIG. 8 through a TSK ™ chromatography column.
Figure 10:
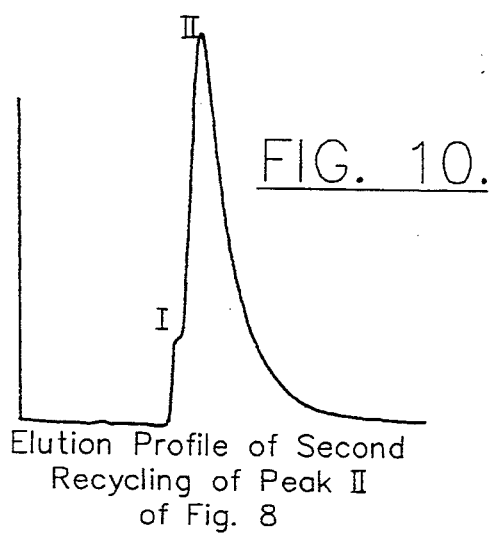

A preparative SPHEROGEL TSK 2000 SW ™ column measuring 21.5 mm by 60 cm is run in 3× phosphate buffered saline at a flow rate of 8 ml per minute to separate the ≧50 k and ≧100 k sera components into the fractions shown in FIG. 4 or FIG. 8. Peak percentages for FIGS. 4 and 8 are given in Tables 1 and 2 below. Note that the time for the elution for peaks will vary slightly depending on experimental parameters such as the use of precolumns and slight variations in buffers. By recycling the greater than 50K fractions back through the column, the peaks I, II, or III are partially isolated one from the other. These are shown in FIG. 5 (Peak I of FIG. 4 at 5.89 minutes), FIG. 6 (peak II of FIG. 4 at 6.71 minutes), and FIG. 7 (peak III of FIG. 4 at 7.86 minutes) respectively. The viral neutralizing activity is located only in Peak II as it was shown to contain the greatest amount of specific activity.

TABLE 1

Peak Percentages for FIG. 4

| Peak | Retention Time | Area Percent | Height Percent |
|---|---|---|---|
| I | 5.88 | 4.2% | 14.3% |
| II | 6.72 | 25.7% | 27.9% |
| III | 7.79 | 58.0% | 46.3% |

TABLE 2

Peak Percentages for FIG. 8

| Peak | Retention Time | Area Percent | Height Percent |
|---|---|---|---|
| I | 5.92 | 2.4% | 10.9% |
| II | 7.02 | 23.6% | 34.0% |
| III | 8.39 | 72.1% | 53.1% |

Figure 11:
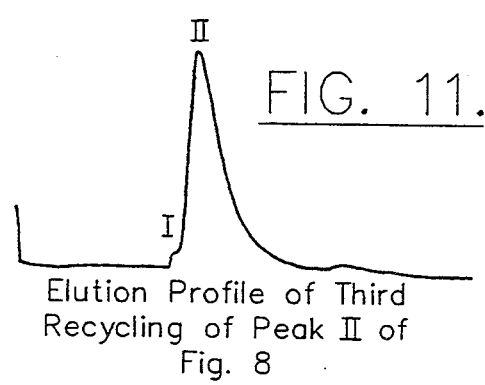

FIGS. 8, 9, 10, and 11 show how Peak II of FIG. 8 is further purified by continued recycling through the TSK ™ column. This mixture of unpurified ≧100 k sera components was initially labelled 5069a, then with further purification, 5070a, 5077a, and finally 5079a, which is the most highly purified form. As shown by the Figures, each time the peak II section eluting from the TSK ™ column is cut and recycled, it becomes further purified and the specific activity is increased. The peak percentages for FIG. 11 are given in Table 3 below. Activity Units for the highly purified IgG fraction containing active VNF are calculated as follows. The ED$_{50}$ titer against IBDV is determined using viral neutralization assays as described below. The ED$_{50}$ titer is the dilution of VNF in 50 μl that will protect 50% of the cells from being killed by the virus. Calculations are based on arbitrarily assigning an ED$_{50}$ dilution titer of 1:25 as being equal to 1 Activity Unit. The actual ED$_{50}$ titer for the specific preparation of VNF is then converted to units per milliliter and finally units per microgram which is defined as the specific activity (see Tables 5–7 for examples of this calculation).

TABLE 3

Peak Percentages for FIG. 11

| Peak | Retention Time | Area Percent | Height Percent |
|---|---|---|---|
| I | 4.91 | .5% | 1.0% |
| II (IgG) | 7.01 | 98.7% | 97.1% |
| IV | 12.39 | .9% | 1.8% |

COMPARATIVE EXAMPLE D

Purity of P-2 Peak I From Comparative Example C by TSK ™ Chromatography

This Example demonstrates the lack of purity in previous preparations of VNF. A stock solution of VNF prepared as described in Comparative Example C above was applied to a TSK chromatography column as described in Example 5 above. The elution profile is given in FIG. 12, and the percentages for each peak is given in Table 4 below. Note that the area percent for IgG is only 18.4%. Compare this Table to Table 3.

TABLE 4

Figure 12:
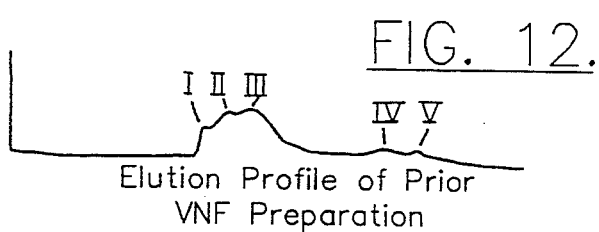
FIG. 12 illustrates, by TSK ™ chromatography, the purity of VNF prepared by prior techniques.

Peak Percentages for FIG. 12

| Peak | Retention Time | Area Percent | Height Percent |
|---|---|---|---|
| I (Macroglobulins) | 5.55 | 5.9% | 18.9% |
| II (IgG) | 6.26 | 18.4% | 28.2% |
| III (Albumin) | 6.86 | 44.1% | 31.0% |
| IV (Low Molecular Weight Contaminant) | 10.51 | 14.3% | 10.0% |
| V (Low Molecular Weight Contaminant) | 11.41 | 15.8% | 9.8% |

EXAMPLE 6

SDS-PAGE of Purified VNF Fractions

SDS-polyacrylamide gel electrophoresis (SDS-PAGE) separations of the most highly purified VNF components obtained in the foregoing Examples conclusively identify VNF as an IgG immunoglobulin.

10 cm by 10 cm gels for SDS-PAGE having a gradient that separates in the 5,000 to 200,000 MW range were obtained from ISS-Enprotech of Hyde Park, Mass., USA. On such gels, Peak II behaves identical to chicken IgG in that it produces 65,000 and 25,000MW components in the presence of 2-mercaptoethanol (2-ME). On such gels, but without 2-ME, Peak II migrates with a major band at about 180,000 MW, as does chicken IgG.

EXAMPLE 7

Chicken Fibroblast Assay

The chicken fibroblast assay is useful as an in vitro screen for identifying VNF activity. It is useful for confirming the purification of VNF from a known source or confirming the presence of VNF in a perspective source. Our assay is based on standard procedures developed by J. Skeeles et al., 23 Avian Dis. 95 (1979). See also *Diseases of Poultry*, 574 (M. Hofstad Ed., 8th ed. 1984). In brief, fibroblasts are harvested from 9–11 day old specific pathogen-free embryos, grown to a thin layer in culture dishes on Complete Minimal Essential Media, and transferred to microtiter plate wells containing Infectious Bursal Disease Virus (Lukert's Strain)

(IBDV). When desired, the IBDV in the microtiter plate is mixed prior to addition of the fibroblast cells with a preparation containing VNF, or suspected of containing VNF, to determine the presence or absence, or degree of, viral neutralizing activity in the preparation. Incubation of IBDV with a prospective neutralizing preparation is carried out for about one hour at 37° C. We determine the end-point of our assay with a MTT Dye reduction assay. Specific aspects of our procedure are given below.

A. Preparation of Fibroblasts for Use in Microtiter Plates.

1. Harvest and culture fibroblasts.
2. After cells have become confluent, remove the media from the tissue culture dishes (Falcon 150×25 mm) and trypsinize with 15-20 mLs of trypsin. Placing the plates in the incubator for 2-5 minutes after adding the trypsin will help the cells to release from the dish quicker than at room temperature.
3. After the cells have released from the dishes, add 5 mLs of Newborn Calf Serum to neutralize the trypsin. Gently swirl the dishes to thoroughly mix the serum with the trypsin.
4. Pipette the trypsin/serum and cells from the dishes into equal aliquots in 50 mL centrifuge tubes. It is helpful to tilt the plate slightly on the side and to rinse the plate with the trypsin/serum mixture to release any adhering cells. Bring the volume of the tubes up to the 40 mL mark with MEM with 5% FCS to neutralize any remaining trypsin.
5. Spin the mixture in the tubes for 10 minutes at 1500 rpm at 16° C.
6. After spinning, pour off the supernatant and add 10 mLs of MEM with 5% FCS to each tube. Mix the cells with a pipette to break up any clumps. Combine all aliquots into one container and mix well.
7. From the combined aliquot, remove a small portion and prepare a 1:10 or 1:20 dilution in MEM with 5% FCS (a 1 mL+9 mL dilution is usually sufficient to get a representative sample, but a 1 mL+19 mL dilution will reduce the number of cells to count).
8. Count the diluted cells on a hemacytometer and dilute in MEM with 5% FCS to make a $0.5 \times 10^6$ cells/mL solution.
9. Add 200 μL of the cell solution to the desired wells of a microtiter plate using a multichannel pipetter. The cell solution must be kept well mixed in order to keep an even dispersal of cells within all the wells. If 15-20 mLs of the cell solution are placed in a sterile petri dish and replenished with freshly mixed cells between each couple of plates, this will help to insure even dispersal of cells into all wells.

B. Incubation of Microtiter plates.

Incubate microtiter plates for 2 days in a 37° C. incubator with 5.5% $CO_2$—Plates may be observed under a microscope after 1-2 days for preliminary test results or to check for visible contamination. Contamination may appear as cloudiness or small black specks in the media.

C. MTT Tetrazolium Dye Reduction Assay for Proliferation or Neutralization.

1. Mix a 5 mg/mL solution of MTT tetrazolium dye (obtained from U.S. Biochemical Corp., Cleveland, Ohio) in 1× PBS. Not all of the crystals will dissolve. Filter sterilize through a 0.45 μm syringe filter under a sterile hood.

2. Under a sterile hood, remove 100 μL of liquid from each well in each plate. "Pulse" the plates by adding 20 μL of MTT to each well after the liquid is removed. Return plates to the incubator for 3 hours.
3. After incubation, remove 100 μL of solution from each well of the plate and discard (this step does not have to be sterile).
4. Add 100 μL of Acid Isopropanol (40 mL 1N HCl or 3.3 mL 12 N HCl in 1 liter isopropanol) to each well.
5. Mix on a shaker for 1 minute at medium high speed (position 6 on a Dynatech Shaker).
6. Read OD within 30 minutes using a wavelength of 570 nm.
7. Calibrate to 0 absorbance with medium +MTT.
8. Read with an appropriate software program (i.e., Immunosoft TM) and template on a microplate reader.

EXAMPLE 8

Viral Neutralizing Activity of Various Serum Fractions Against Infectious Bursal Disease Virus in the Chicken Fibroblast Assay The various serum fractions described in Examples 3 to 6 above were tested for activity against IBDV in accordance with the procedures described in Example 7 above. These data are given in Tables 5 and 6 below. Peak II was the only fraction containing the majority of viral neutralizing activity. In all cases, the specific activity was greatest for Peak II and greatest for the most highly purified form of peak II (5079b, peak II—Table 7, or 5079a—Table 8). The relative percentage of active VNF contained in the peak II IgG fraction varies from one serum preparation to another. FIG. 3 and FIGS. 8-11 show the purification scheme and profiles of purifying the IgG fraction containing VNF. Tables 5-7 show the activities of various fractions from the TSK2000 column. Fraction 5079a activity is shown in Table 8. This 5079a fraction was fractionated into 5079b, peak I, which contained very low levels of macroglobulin contaminants, and 5079b, peak II, which contained the IgG fraction. Table 7 shows that 5079b, peak II contains the VNF activity.

TABLE 5

Virus Neutralization Activity of High and Low Molecular Weight Serum Factors Against Infectious Bursal Disease Virus (IBDV)[1,2,3]

| Sample # | Origin | Titer ED50 | Units/ 50 μl | Units/ ml[4] | Protein (μg/ml) | Specific Activity (Units/μg) |
|---|---|---|---|---|---|---|
| 5046 | ≧50K (S)[5] | 11,220 | 448.8 | 8976 | 60,350 | .1 |
| 5*21 | Peak I-TSK | 22.4 | .89 | 20 | 123 | .2 |
| 5*221 | Peak II-TSK | 25.7 | 1.02 | 21 | 26 | .8 |
| 5*332 | Peak III-TSK | 4 | .16 | 3.2 | 110 | .0 |
| 5061 | ≧100K (S) | 1,778 | 71 | 1422 | 19,120 | .1 |
| 5062 | ≧100K (S) | 2 | .08 | 1.6 | 90 | .0 |
| 5032 | ≦20K (Sar)[5] | 46.7 | 1.86 | 37.3 | 660 | .1 |

[1]HyVAC chicken fibroblasts at 1 × 10⁵ cells/well in 200 μl volume were used in assay.
[2]Various fractions were tested in 5 fold dilutions through 1:15,625 in 50 μl volumes/well.
[3]Virus used was Leukerts Strain IBDV at 1:100 dilution in 50 μl volume well.
[4]Calculations based on 1:25 dilution = 1 unit of activity in 50 μl volume.
[5]S = SPECTRUM TM Hollow Fiber, Sar = Sartorious membrane system.

TABLE 6

Virus Neutralization Activity of Various Serum Fractions Against Infectious Bursal Disease Virus (IBDV) With Increased Purification of Active Factor

| Sample # | Origin | Titer ED50 | Units/ 50 μl | Units/ ml | Protein (μg/ ml) | Specific Activity (Units/ μg) |
|---|---|---|---|---|---|---|
| 5069 | ≧100K (I, II, III) | 17,782 | 711.3 | 14,226 | 90,443 | .2 |
| 5070 | Peaks I, II, III (1st TSK) | 4,168 | 166.7 | 3,334 | 12,923 | .3 |
| 5077 | Peak II (2nd TSK) | 1,000 | 40 | 800 | 1,073 | .7 |
| 5075 | HMW ≦20K Sartorious | 123 | 4.9 | 98 | 255 | .4 |
| P2 | Comp. Ex. C | 60.2 | 2.4 | 48 | 91 | .5 |

TABLE 7

Virus Neutralization Activity of Chicken Sera Factors at Various Stages of Purification Against Infectious Bursal Disease Virus

| Sample # | Origin | Titer ED50 | Units/ 50 μl | Units/ ml[4] | Protein (μg/ ml) | Specific Activity (Units/ μg) |
|---|---|---|---|---|---|---|
| 5079b (I) | Further purified 5079a into peak I | 354 | 14 | 280 | 5,400 | .1 |
| 5979b (II) | Further purified 5079a into peak II (IgG) | 316 | 12.6 | 252 | 350 | .7 |
| 5069a | (I, II, III) ≧100K (S) | 16,982 | 679 | 13,580 | 90,443 | .2 |
| 5070a | I, II, III (1st TSK Prep) | 12,589 | 503 | 10,060 | 34,125 | .3 |
| 5077a | II- (2nd TSK Prep) | 5,011 | 200 | 4,000 | 6,720 | .6 |

EXAMPLE 9

Viral Neutralizing Factor Found in Sera From Other Regressor Lines of Chickens with the Chicken Fibroblast Assay These experiments were carried out in essentially the same manner as the experiments described in Example 8 above, except that alternate sources for Viral Neutralizing Factor were tested. The data for these experiments are given in Table 8 below. Table 8 also compares the regressor sera with HyLine sera. These data indicate that sera from the East Lansing regressor lines of chickens tested do not contain significant VNF activity. In addition, it was found that Sera from unchallenged Arkansas Regressor birds contains VNF, and that sera from challenged Arkansas Progressor chickens contains VNF-like activity comparable to challenged Arkansas Regressor chickens.

TABLE 8

Virus Neutralization Activity of Chicken Sera From Various Genetically Different Lines of Chickens Against Infectious Bursal Disease Virus

| Sample # | Origin | Titer ED50 | Units/ 50 μl | Units/ ml[4] | Protein (μg/ ml) | Specific Activity (Units/ μg) |
|---|---|---|---|---|---|---|
| 5079a | Control Peak | 625 | 25 | 500 | 650 | .8 |
| Progressor sera #4565 | ARK Challenged | 3,548 | 142 | 2,838 | | |
| Progressor sera #676 | ARK Unchallenged | 20 | 0.8 | 16 | | |
| Regressor sera #194 | ARK Unchallenged | 1,258 | 50 | 1,000 | | |
| Regressor sera | (Challenged Boost) | 3,162 | 126.4 | 2,528 | 27,430 | .1 |
| HyLine sera | (Challenged RSV 1st) | 1 | .04 | .8 | 24,250 | |
| East Lansing 12733 | 15.C-12 × C | 0 | 0 | 0 | | |
| East Lansing 13133 | 15.C × 12 | 0 | 0 | 0 | | |
| East Lansing | 6.3 × 15.6 | 35 | 1.4 | 28 | | |

TABLE 8-continued

Virus Neutralization Activity of Chicken Sera From Various Genetically Different Lines of Chickens Against Infectious Bursal Disease Virus

| Sample # | Origin | Titer ED50 | Units/ 50 μl | Units/ ml[4] | Protein (μg/ml) | Specific Activity (Units/μg) |
|---|---|---|---|---|---|---|
| 12772 East Lansing | | 6.3 | 0 | 0 | 0 | |
| 12760 East Lansing | | 15.6 × 2 | 0 | 0 | 0 | |
| 12792 | | | | | | |

EXAMPLE 10

Protection of Chicks at Hatch from Live Virus Administered In Ovo with VNF

This experiment demonstrates that VNF protects chickens at hatch from IBDV given as a vaccine in ovo at day 18 of incubation. Note that existing vaccine strains of IBDV are so infectious that they are difficult to use in ovo without severe reductions in hatchability.

The procedure described herein also provides a test for conjugates capable of serving as a vaccine.

The study consisted of 9 groups with 10–15 HYVAC embryonated eggs in each group. Standard vaccine against IBDV was provided by CEVA Laboratories, IBD-BLEN TM (1000 doses/vial). Doses of 10X, 1X, 0.1X, and 0.01X of vaccine per 50μl volume were prepared. VNF was used at 800 μg/50μl volume as a 1X dose and doses of VNF were prepared in 1X (800μg) and 0.1X dose (80 μg)/50μl amounts. For in ovo injection 50μl IBD-BLEN TM and 50μl VNF were mixed and made up to 200μl total volume using CEVA diluent. Various doses of IBD-BLEN TM plus VNF were administered as vaccines, and various doses of IBD-BLEN TM vaccine alone were used to vaccinate the 18 day old embryos. Table 9 lists the vaccine treatments that the various groups received. The birds were allowed to hatch and were grown out in separate groups to day 5 post hatch. At this time the birds were weighed and the bursas weighed and examined.

Nine groups of bursas, three per group, were submitted for histological evaluation. These tissues were graded in the following manner: 0=normal; 1=minimal change (which includes slight irregularity to the surface mucosa, some depletion of lymphocytes in some follicles with the normal size); 2=mild changes—mild invaginations, with some depletion of lymphocytes and some atrophy of the follicles (this will also include some inflammatory changes with no necrosis); 3=moderate changes—more extensive invagination of the mucosa with the folds being reduced in size (most follicles will be atrophic and/or depleted or lymphocytes, more extensive inflammation or necrosis); 4=extensive changes—folds obviously atrophied (inter-follicular epithelium will be depressed in the folds causing some vacuole-like formation. This will include no normal follicles with more extensive inflammation or necrosis); 5=severe—normal architecture is severely disrupted, folds markedly reduced in size. This may also include extensive inflammation or necrosis.

Tables 9 and 10 show the body weight gains, percentage of hatch, bursal weight, and bursa histology among various groups. Birds receiving the 10X dose IBD-BLEN TM +1X dose VNF showed significantly greater hatchability (100%) than those receiving the 10X dose of IBD-BLEN TM alone (55%). The same was true at the 1X vaccine dose level. Body weight gain was decreased (5 to 9 grams) in birds receiving the 1X, 0.1X, and 0.01X IBD-BLEN TM vaccine dose alone (Table 11) when compared to uninoculated controls (14.8 grams). However, when VNF was added to these same doses of IBD-BLEN TM, the body weight gain was significantly increased (17 to 18 grams).

Essentially the same effect was seen on bursa weight as on body weight gain. The IBD-BLEN TM doses alone produced bursal atrophy and bursa weight loss (0.04 to 0.06 gram) by day 5 when compared to controls (0.13 gram). The addition of VNF with vaccine resulted in bursas with normal weight (0.12 to 0.15 gram) (Table 10). However, the bursal histology showed that a ratio in the vaccine of 1X virus to 10X VNF was required to more completely protect the bursa from IBDV infection. A 1X virus to 1X VNF ratio with vaccine protected hatchability, body weight gain, and bursal weight, but did not prevent some unneutralized virus from causing bursal lymphocyte depletion (Table 10).

TABLE 9

In Ovo Vaccination with IBD-BLEN TM and VNF and Effect on Hatchability and Body Weight Gain from Day 0 to Day 5

| | Mean Body Weight (g) | SEM | n | % Hatch |
|---|---|---|---|---|
| PERCENT HATCH AND BODY WEIGHT GAIN FROM DAY 0 TO DAY 5 | | | | |
| IBD-BLEN TM 10X[1] | . | . | 1 | 55 |
| IBD-BLEN TM 10X + VNF-1(1X)[2] | 11.39$^{BC}$ | 1.91 | 11 | 100 |
| IBD-BLEN TM 1X | 5.01$^{D}$ | 2.55 | 10 | 83 |
| IBD-BLEN TM 1X + VNF-1(1X) | 18.33$^{A}$ | 1.49 | 11 | 92 |
| IBD-BLEN TM .1X | 7.70$^{CD}$ | 1.53 | 9 | 91 |
| IBD-BLEN TM .1X + VNF-2(.1X) | 16.43$^{A}$ | 1.64 | 10 | 91 |
| IBD-BLEN TM .01X | 8.99$^{CD}$ | 1.26 | 10 | 91 |
| IBD-BLEN TM .01X + VNF-2(.1X) | 17.52$^{A}$ | 1.50 | 10 | 100 |
| Positive Control (No Vaccination) | 14.80$^{AB}$ | 1.21 | 11 | 100 |

Treatment was significant at the .05 level for groups with different superscripts.
[1] A 1X dose of IBD-BLEN represents ED$_{50}$ titer value of 1:500.
[2] A 1X dose of VNF represents 800 μg/dose.

TABLE 10

In Ovo Vaccination with IBD-BLEN ™ and VNF and Effect on Bursa Weight and Histology

| | Mean Bursal Weight (g) | SEM | n | Bursa Histology Scores |
|---|---|---|---|---|
| IBD-BLEN ™ 10X | . | . | 1 | 3,3 |
| IBD-BLEN ™ 10X + VNF-1(1X) | $.07^B$ | .01 | 11 | 3,3,3 |
| IBD-BLEN ™ 1X | $.04^B$ | .00 | 10 | 3,4,4 |
| IBD-BLEN ™ 1X + VNF-1(1X) | $.12^A$ | .02 | 11 | 3,3,3 |
| IBD-BLEN ™ .1X | $.06^B$ | .00 | 9 | 3,4,3 |
| IBD-BLEN ™ .1X + VNF-2(.1X) | $.11^A$ | .01 | 10 | 3,3,4 |
| IBD-BLEN ™ .01X | $.06^B$ | .01 | 6 | 3,3,5 |
| IBD-BLEN ™ .01X + VNF-2(.1X) | $.15^A$ | .02 | 6 | 0,0,2 |
| Positive Control | $.13^A$ | .01 | 8 | 0,0,1 |

Treatment was significant at the .05 level for groups with different superscripts.

EXAMPLE 11

Immunization of Chicks by Administration of VNF and Live Virus In Ovo

This Example extends Example 10 above by demonstrating that a VNF-IBDV conjugate actually immunizes chickens against Infectious Bursal Disease Virus (IBDV). In this experiment, VNF was preincubated with CEVA IBD-BLEN ™ vaccine, the vaccine provided at recommended and less than optimal concentrations, and the mixture administered in ovo to embryonated eggs prior to live challenge with USDA-IBDV at day 39 post vaccination (or day 35 post hatch).

The study consisted of ten groups. HYVAC eggs were used in Groups 1–6 and SPAFAS eggs were used in Groups 7–10. Each group was housed in a separate isolation unit and all units were located in the same room. Treatments differed by materials being administered and by methods of administration. Treatment groups, doses, and sample sizes are given in Table 11 below.

Baseline data was collected from positive control groups (Groups 1 and 7), and from negative control groups (Groups 2 and 8). Fertile, viable SPAFAS-SPF and HYVAC eggs were vaccinated by in ovo manual injection on Day 18 of incubation. Injection was through the top of the egg into the amnion. The volume of injection was 200 μl. Parameters measured were hatchability, hatch weight, IBD antibody titer, body weight, bursa weight, and bursa histology.

TABLE 11

Treatment Groups, Doses, and Sample Sizes

| Group No. | Treatment Description | CEVA Vaccine Dose In Ovo | USDA-IBDV Dose (PFU) Day 35 Post Hatch | VNF Dose (μg) | Est. # of Eggs |
|---|---|---|---|---|---|
| HYVAC EGGS | | | | | |
| 1 | Positive Control | | 47 | | 21 |
| 2 | Negative Control IBD-BLEN ™ Vaccine (1X)[1] | 1X | 47 | | 38 |
| 3 | IBD-BLEN ™ (1X) + VNF (Dose 1)[2] | 1X | 47 | 800 | 22 |
| 4 | IBD-BLEN ™ (1X) + VNF (Dose 2) | 1X | 47 | 80 | 22 |
| 5 | IBD-BLEN ™ (1X) + VNF (Dose 3) | 1X | 47 | 8 | 38 |
| 6 | VNF Alone (Dose 1) | | 47 | | 21 |
| SPAFAS EGGS | | | | | |
| 7 | Positive Control | | 47 | | 25 |
| 8 | Negative Control IBD-BLEN ™ Vaccine (.1X) | .1X | 47 | | 25 |
| 9 | IBD-BLEN ™ (.1X) + VNF (Dose 1) | .1X | 47 | 800 | 25 |
| 10 | IBD-BLEN ™ (.1X) + VNF (Dose 2) | .1X | 47 | 80 | 25 |

[1] A 1X dose (or standard dose) of IBD-BLEN ™ represents an $ED_{50}$ titer value of 1:500.
[2] VNF dose 1 = 1 standard VNF dose (800 μg/dose), VNF dose 2 = .1X standard VNF dose, and VNF dose 3 = .01X standard VNF dose.

The results of this experiment are illustrated in Tables 12 to 15 below. HYVAC birds that received VNF mixed with IBD-BLEN ™ demonstrated increased hatchability (82%) as compared to those that received vaccine alone (32%), and better hatchability was seen at the higher concentrations of VNF (82–47%) (Table 12). The SPAFAS hatchability cannot be compared (Table 12) due to other problems encountered during hatch. However, those remaining alive for the rest of the study represent reliable birds for examination of study parameters. Mortality to day 35 was greater in those groups receiving vaccine alone or in vaccine combination with the lower doses of VNF (Table 12). Higher doses of VNF protected against high mortality when mixed with the vaccine (data was similar to controls).

HYVAC birds that received VNF mixed with IBD-BLEN ™ showed normal weight gain (45–59 grams) after challenge with USDA-IBDV but the nonvaccinated birds showed low weight gain (5.6 grams) (Table 13). Vaccination with VNF alone did not offer protection against the USDA challenge. Also, mortality for these groups was reduced when compared to unvaccinated controls (Table 12).

In general, a higher VNF to virus ratio offered increased protection to the bursa after USDA challenge (Table 14). Control bursas receiving no vaccine were severely hemorrhagic and edemic after challenge (Table 14). Birds receiving vaccine alone had severely atrophied bursas, and birds receiving vaccine and VNF had partially atrophied bursas after challenge.

Birds that were vaccinated with the mixture of IBD-BLEN TM and VNF showed significantly greater antibody titers to USDA-IBDV challenge than those receiving the IBD-BLEN TM alone (Table 15). This indicates that these birds would have carried a much higher protection after vaccination to any secondary infections throughout growout as compared to those receiving the virus vaccine alone. Again, one can see that antibody titer begins to fall off at the lowest dose of VNF when mixed with virus. This indicates that, if too much damage is caused to the bursa at vaccination, protection in terms of antibody titer is lost throughout the rest of the life of the bird.

TABLE 12

In Ovo Vaccination with IBD-BLEN TM and VNF and Effect on Hatchability and Mortality

| Group No. | Hatchability | | Mortality by D35 | | Mortality Post Chal | |
|---|---|---|---|---|---|---|
| | n | % | n | % | n | % |
| 1 | 16/21 | 76.2$^A$ | 0/16 | 0.0$^A$ | 7/16 | 43.8$^B$ |
| 2 | 12/38 | 31.6$^B$ | 4/12 | 33.0$^A$ | 0/8 | 0.0$^B$ |
| 3 | 18/22 | 81.8$^A$ | 0/18 | 0.0$^A$ | 1/18 | 5.6$^B$ |
| 4 | 16/22 | 72.7$^A$ | 1/16 | 6.3$^A$ | 0/15 | 0.0$^B$ |
| 5 | 18/38 | 47.4$^{AB}$ | 5/18 | 27.8$^A$ | 1/13 | 7.7$^B$ |
| 6 | 15/21 | 71.4$^{AB}$ | 0/15 | 0.0$^A$ | 2/15 | 13.3$^B$ |
| 7 | 13/25 | 52.0$^a$ | 7/13 | 53.8$^{ab}$ | 1/6 | 16.6$^A$ |
| 8 | 11/25 | 44.0$^a$ | 10/11 | 90.9$^a$ | 0/1 | 0.0$^A$ |
| 9 | 7/25 | 28.0$^a$ | 1/7 | 14.3$^b$ | 0/6 | 0.0$^A$ |
| 10 | 8/25 | 32.0$^a$ | 0/8 | 0.0$^b$ | 0/8 | 0.0$^A$ |

Different superscripts designate significant differencies by chi square analysis.

TABLE 13

In Ovo Vaccination with IBD-BLEN TM and VNF and Effect on Body Weight Gain of SPF Chickens After USDA-IBDV Challenge on Day 35 Post Hatch

| Group No. | Mean (g) | SEM | n |
|---|---|---|---|
| WEIGHT GAIN FROM DAY 35 TO DAY 39 | | | |
| 1 | 5.61$^B$ | 6.99 | 9 |
| 2 | 59.29$^A$ | 3.63 | 8 |
| 3 | 45.66$^A$ | 1.81 | 17 |
| 4 | 56.26$^A$ | 2.94 | 15 |
| 5 | 50.28$^A$ | 5.98 | 12 |
| 6 | 16.33$^B$ | 4.80 | 13 |
| 7 | 18.20$^c$ | .62 | 5 |
| 8 | 57.90 | | 1 |
| 9 | 43.35$^b$ | 6.26 | 6 |
| 10 | 62.60$^a$ | 4.64 | 8 |

Means with different superscripts differed significantly at the .05 level. (The SPAFAS .1X treatment was not included in the statistical analyses).

TABLE 14

Bursa Weight of SPF Chicken Groups After In Ovo Vaccination and Day 35 Post Hatch USDA-IBDV Challenge

| Group No. | Mean (g) | SEM | n |
|---|---|---|---|
| BURSA WEIGHT DAY 39 | | | |
| 1 | 2.03$^A$ | .29 | 9 |
| 2 | .55$^B$ | .20 | 8 |
| 3 | .73$^B$ | .07 | 17 |
| 4 | .62$^B$ | .12 | 15 |
| 5 | .47$^B$ | .09 | 12 |
| 6 | 2.05$^A$ | .11 | 13 |

TABLE 14-continued

Bursa Weight of SPF Chicken Groups After In Ovo Vaccination and Day 35 Post Hatch USDA-IBDV Challenge

| Group No. | Mean (g) | SEM | n |
|---|---|---|---|
| 7 | 2.28$^a$ | .23 | 5 |
| 8 | .29 | — | 1 |
| 9 | .57$^b$ | .11 | 6 |
| 10 | .77$^b$ | .12 | 8 |

Means with different superscripts differed significantly at the .05 level. (The SPAFAS .1X treatment was not included in the statistical analyses).

TABLE 15

In Ovo Vaccination with IBD-BLEN TM and VNF and Effect on Antibody Titer After USDA-IBDV Challenge TITERS (LOG 10)

| Group No. | Mean | SD | SEM | n | Inverse Log Mean Titer |
|---|---|---|---|---|---|
| 1 | .66$^C$ | .71 | .24 | 9 | 4.57 |
| 2 | 2.15$^B$ | .93 | .33 | 8 | 141.25[1] |
| 3 | 3.33$^A$ | .29 | .07 | 17 | 2137.96[2] |
| 4 | 3.31$^A$ | .40 | .10 | 15 | 2041.74 |
| 5 | 2.95$^A$ | .76 | .22 | 12 | 891.25 |
| 6 | .61$^C$ | .59 | .17 | 12 | 4.07 |
| 7 | .85$^b$ | .54 | .24 | 5 | 7.08 |
| 8 | .30 | .00 | .00 | 1 | 2.00 |
| 9 | 3.30$^a$ | .20 | .08 | 6 | 1995.26 |
| 10 | 3.25$^a$ | .62 | .22 | 8 | 1778.28 |

Means with different superscripts differed significantly at the .05 level.
[1]In Group 2, 13% of the birds had titers greater than 1,000 and 87% had titers less than 1,000.
[2]In Group 3, 82% of the birds had titers greater than 1,000 and only 18% had titers less than 1,000.

EXAMPLE 12

Alternate Sources of VNF as Determined by the Chicken Fibroblast Assay

This Example demonstrates alternate sources of VNF with the chicken fibroblast assay described in Example 7 above.

Table 16 illustrates the viral neutralization titers against IBDV of serum samples from various birds as well as the corresponding Elisa titers. From this data one can see that some serum samples (HyLine chicken) have very high Elisa titers with correspondingly low viral neutralization titer. Hence, it is possible to have antibodies that bind very strongly to IBDV but do not neutralize IBDV. The HyLine chicken was challenged with RSV, regressed tumors, and produced binding antibodies against IBDV, but did not produce viral neutralizing antibodies against IBDV. The Arkansas regressor line chicken serum sample has both binding and neutralizing activity against IBDV.

An interesting observation is that unchallenged Jungle Fowl chickens from both the University of Arkansas and Mississippi State University produce serum with neutralizing antibodies against IBDV. Note also that Table 16 shows that VNF-like activity is found in the serum of a SPAFAS chicken that was innoculated with IBDV.

TABLE 16

Viral Neutralizing Activity and Elisa Titer of Various Serum Samples, VNF (5077D), and SPAFAS IBDV Antisera Against IBDV

| Sample Origin | ED$^{50}$ Titer | Units 50 µl | Units/ ml | Units/ ml[1] | Elisa Titer |
|---|---|---|---|---|---|
| VNF Peak II - TSK (1:4 dilution) (5077 D) | 2,238 | 89.5 | 1,790 | 7,161 | 102,400 |
| SPAFAS IBDV | 251 | 10 | 200 | 20,000 | 81,800 |

TABLE 16-continued

Viral Neutralizing Activity and Elisa Titer of Various Serum Samples, VNF (5077D), and SPAFAS IBDV Antisera Against IBDV

| Sample Origin | $ED^{50}$ Titer | Units 50 μl | Units/ ml | Units/ ml[1] | Elisa Titer |
|---|---|---|---|---|---|
| Antisera (1:100 dilution) | | | | | |
| University of Arkansas Jungle Fowl (1:10 dilution) | 398 | 15.9 | 318 | 3,180 | 25,600 |
| University of Arkansas Regressor line sera (1:10 dilution) | 112 | 4.5 | 90 | 900 | 12,800 |
| Mississippi State University Jungle Fowl sera (1:10 dilution) | 316 | 12.6 | 252 | 2,520 | 12,800 |
| HyLine SC Line sera (1:5 dilution) | 3.1 | .12 | 2.4 | 12 | 819,200 |
| Unchallenged University of Arkansas (1:5 dilution) Progressor line sera | 3.9 | .15 | 3 | 15 | 12,800 |
| Challenged University of Arkansas (1:5 dilution) Progressor line sera | 501 | 20 | 400 | 2,000 | 12,800 |

[1]Units corrected for dilution of original sample.

EXAMPLE 13

In Situ Vaccination Potential of VNF with Infectious Bursal Disease Virus

The object of this experiment was to test the efficacy of the VNF-IBD-BLEN TM mixture when administered by IM injection to chickens on 1-2 day post hatch to stimulate immunity to a secondary challenge of USDA-IBDV challenge virus.

Approximately 160 healthy 1 or 2 day old Hy-Vac chickens that are very susceptible to IBD-BLEN TM strain and are typically used in regulatory studies for licensing vaccines were used. Challenge of vaccinated birds was carried out with USDA Challenge Strain of Infectious Bursal Disease Virus (USDA-IBDV-CV) Lot #83-1, $10^{3.8}$ $EID_{50}$/ml. Standard vaccine against IBDV was obtained from SANOFI (IBD-BLEN TM) at 1000 doses/vial, $10^{2.7}$ $EID_{50}$/dose. VNF from Arkansas regressor line birds as prepared as described above, 16,000μg/ml in 1.5X Phosphate Buffered Saline, (PBS) pH 7.4. Its activity is determined by its viral neutralizing activity against Lukert's Strain of IBDV using Hy-Vac chicken fibroblasts in microneutralization assays. Purity was checked by HPLC.

Each chicken receiving the IBD-BLEN TM 1X or 0.1X dose vaccine received 100μl of the IBD-BLEN TM preparation by IM injection into the thigh of the left leg. The 100 μl total volume will be composed of 50 μl IBD-BLEN TM (1X or 0.1X)+50 μl CEVA diluent. (Group.2 - 1X dose, Group 5-0.1X dose).

Each chicken receiving the IBD-BLEN TM 1X+VNF (Dose 1 or Dose 2) or 0.1X+VNF (Dose 1), received 100 μl of the vaccine mixture by IM injection. The 100 μl total volume was composed of 50 μl IBD-BLEN TM (1X or 0.1X)+50 μl VNF (Dose 1 or Dose 2). (Group 3 —IBD-BLEN TM (1X)+VNF —Dose 1, Group 4 —IBD-BLEN TM (1X) +VNF - Dose 2, Group 6 —IBD-BLEN TM (0.1X) +VNF—Dose 1).

Each chicken receiving the VNF alone received 100μl of the VNF preparation by IM injection. The 100μl total volume will be composed of 50μl VNF—Dose 1+50μl CEVA diluent. (Group 7).

Each chicken receiving the USDA-IBDV challenge virus on Day 21 post vaccination will receive 30 μl of the preparation by eye drop in each eye. The 60 μl total volume required for both eyes is composed from a preparation of 1:8 dilution of stock USDA-IBDV virus which is 6309 $EID_{50}$/ml. (1.4ml USDA-IBDV +9.8ml CEVA diluent—23.5 $EID_{50}$/30μl)

Data from this experiment are given in Table 17 below. Note that the birds in group 6 showed protection by day 10 from the vaccine virus in the virus-VNF conjugate. Hence, data from this study shows that it is possible to neutralize or inhibit a 0.1X dose of IBD-BLEN TM with 136 units of VNF so as to protect the bursa from the virus in the virus-VNF conjugate until day 10. Furthermore, when these birds are challenged on day 29 with USDA challenge strain, they show protection (no body weight loss, no mortality) from the challenge.

TABLE 17

Summary of Body Weight Gain, Bursa Parameters, and IBD Antibody Titers for Example 13

| Treatment Group | VNF Units/ 50 μl | Number Birds/ Group | Body Weight Gain Day 0-35 | Body Weight Gain Day 35-40 | Average Bursal Weight (gr) Day 10 | Average Bursal Weight (gr) Day 35 | Average Bursal Weight (gr) Day 40 | Percent Lymphocytes Remaining in Bursa Day 10 | Percent Lymphocytes Remaining in Bursa Day 40 | IBDV Antibody Titer (% Hi) Day 10 | IBDV Antibody Titer (% Hi) Day 35 | IBDV Antibody Titer (% Hi) Day 40 | Percent Mortality Day 35-40 |
|---|---|---|---|---|---|---|---|---|---|---|---|---|---|
| SPF | | | | | | | | | | | | | |
| 1 Control | | 7 | $^A$401 | $^D$−9 | $^{AB}$.45 | 2.7 | $^A$2.1 | 100 | 0 | $^B$5 | $^B$41 | $^C$419 | 50 |
| 2 VACC 1X | | 22 | $^C$337 | $^C$44 | $^C$.12 | | $^B$.8 | 20 | 60 | $^A$347 | $^A$1664(40) | $^B$1763(50) | 0 |
| 3 VACC 1X VNF-1 (800 μg) | 136 | 13 | $^{AB}$381 | $^{BC}$49 | $^{AB}$.50 | | $^B$.7 | 35 | 38 | $^B$2 | $^A$3105(90) | $^A$3778(92) | 0 |
| 4 VACC 1X VNF-2 (80 μg) | 14 | 16 | $^{ABC}$365 | $^{AB}$59 | $^C$.15 | | $^B$.6 | 0 | 40 | $^A$158 | $^A$2172(60) | $^{AB}$3163(68) | 0 |
| 5 VACC .1X | 23 | | $^{AB}$372 | $^{BC}$55 | $^C$.13 | | $^B$1.0 | 5 | 78 | $^A$467 | $^A$1805(75) | $^{AB}$2705(77) | 0 |
| 6 VACC .1X VNF-1 (800 μg) | 136 | 13 | $^A$379 | $^A$69 | $^A$.58 | | $^B$.5 | 90 | 15 | $^B$2 | $^A$2885(60) | $^A$4255(81) | 0 |
| 7 VNF-1 | 136 | 15 | $^{BC}$343 | $^D$6 | $^B$.39 | | $^A$1.6 | 100 | 0 | $^B$3 | $^B$41 | $^D$78 | 10 |

TABLE 17-continued

Summary of Body Weight Gain, Bursa Parameters, and IBD Antibody Titers for Example 13

| Treatment Group | VNF Units/ 50 μl | Number Birds/ Group Day 40 | Body Weight Gain Day 0-35 | Body Weight Gain Day 35-40 | Average Bursal Weight (gr) Day 10 | Average Bursal Weight (gr) Day 35 | Average Bursal Weight (gr) Day 40 | Percent Lymphocytes Remaining in Bursa Day 10 | Percent Lymphocytes Remaining in Bursa Day 40 | IBDV Antibody Titer (% Hi) Day 10 | IBDV Antibody Titer (% Hi) Day 35 | IBDV Antibody Titer (% Hi) Day 40 | Percent Mortality Day 35-40 |
|---|---|---|---|---|---|---|---|---|---|---|---|---|---|
| (800 μg) | | | | | | | | | | | | | |

(%) = % of birds with ≧1000 IBDV antibody titer
$^{ABCD}$Means with different superscripts differed significantly at the .05 level.

EXAMPLE 14

In situ Vaccination Potential of HyLINE Sera with SANOFI IBD-BLEN TM Vacine When Administered Subcutaneously to HyVAC SPF Chickens The object of this experiment was to evaluate immunological and pathological changes in terms of antibody titers and bursa parameters at 21 days of age in chickens receiving inoculations of SANOFI IBD-BLEN TM that has been incubated with SC HyLINE sera and administered as a complete vaccine conjugate subcutaneously into the bird's neck.

Healthy one (1) day old HyVAC SPF chickens (about 90 total) that are susceptible to IBD-BLEN TM vaccination and USDA-IBDV challenge where used in these studies.

SC-Sera ($\approx$35,000μg/ml, #SC-2-22-90, ED$_{50}$/ml of 1:3,000,000) is whole sera which contains VNF and is produced by boosting SC HyLINE chickens with SANOFI IBD-BLEN TM in accordance with known procedures. VNF activity in this sera is determined by vital neutralization assays as described above.

IBD-BLEN TM, and SC HyLINE sera where stored at 4° C. until ready for use. Once prepared, the IBD-BLEN TM vaccine and Sera-IBD-BLEN TM, mixtures where held at room temperature for one (1) hour before inoculation.

Data for the various experimental and control groups in this study are given in Table 18. These data demonstrate that, at concentrations of VNF equal to or greater than 316 Units, the bursa can be protected by weight at day 22 from the vaccine virus in the vaccine serum conjugate given at day 1.

EXAMPLE 15

Minimum Protective Dose of SC HyLINE Serum with Infectious Bursal Disease Virus Vaccine Administered Subcutaneously to HFVAC SPF Chickens SANOFI IBD-BLEN TM is a virulent live virus vaccine capable of causing acute and chronic bursal lesions 3-9 days post vaccination in SPF chickens. Previous experiments utilizing this vaccine in 1 to 2 day old HyVAC SPF chickens have demonstrated bursal atrophy by day 10 to day 14 from intramuscular and subcutaneous inoculations of 1X through 0.0001X doses of IBD-BLEN TM.

In this study, certain groups of one (1) day old HyVAC SPF chickens where vaccinated subcutaneously with various doses of SANOFI IBD-BLEN TM alone and in combination with various doses of SC HyLINE serum containing VNF. Vaccinated and control chickens where examined for bursal morphology as well as gross lesions at 15 or 22 days of age and challenged at 29 days of age with USDA-IBDV challenge strain to confirm immunogenicity (14, 21, and 28 days post vaccination). The object of this experiment is to evaluate immunological and pathological changes in terms of antibody titers and bursa parameters at 15 and 22 days of age in chickens receiving inoculations, at one (1) day of age (14, 21, and 28 days post vaccination), of various doses of SANOFI IBD-BLEN TM alone and incubated with various doses of SC HyLINE serum and administered as a complete vaccine. USDA-IBDV challenge occured at 29 days of age.

Healthy one (1) day old HyVAC SPF chickens (630) that are susceptible to IBD-BLEN TM vaccination and USDA-IBDV challenge where used in this study. SC-Serum (40,000μg/m , #5-18-90, ED$_{50}$/ml of

TABLE 18

Day 1 Posthatch Dose Titration Vaccination in SPF Chickens Using SANOFI IBD-BLEN TM Plus Viral Neutralization Factor (VNF) and Evaluation of Bursal Parameters at Day 21 Posthatch (Example 14)

| Group Number | IBDV-BLEN TM Dose[1] | VNF Units[2] | Body Weight | Bursa Weight | Relative Bursa Weight (g/kg) | Bursal Index | Titer Log-10 | Titer INV Log |
|---|---|---|---|---|---|---|---|---|
| 15 | Negative Control | | A 178.8 | A 1.07 | A 5.94 | A 100.00 | C .52 | 3 |
| 16 | .01X | 0 | A 168.67 | B .27 | B 1.57 | B 26.44 | A 3.10 | 1259 |
| 17 | .01X | 3159 | A 177.4 | A 1.06 | A 5.73 | A 96.48 | B 1.0 | 11 |
| 18 | .01X | 316 | A 178.8 | A 1.01 | A 5.61 | A 94.48 | C .30 | 2 |
| 19 | .01X | 32 | A 157.0 | B .25 | B 1.63 | B 27.53 | A 2.63 | 427 |
| 20 | .01X | 3.2 | A 173.1 | B .25 | B 1.44 | B 24.29 | A 2.67 | 468 |

A, B, C = Means in a column processing different superscripts differed significantly at the .05 level
[1] 1 0.01X dose of SANOFI IBD-BLEN TM is 2.24 EID50/dose (Lot #29967).
[2] Viral neutralization activity expressed as units/50 μl dose.

≈1:511,000) is whole serum which contains VNF and is produced by boosting SC HyLINE chickens with SANOFI IBD-BLEN ™. VNF activity in this serum is determined by viral neutralization assays as described above. Commercial vaccine against IBDV, IBD-BLEN ™, was provided by SANOFI Laboratories at 1000 doses/vial, $10^{2.3}$ $EID_{50}$ titer. USDA-Challenge Strain of Infectious Bursal Disease Virus, Lot #83-3,$10^{3.8}$ $EID_{50}$/ml, was used as a challenge. Vaccination was by subcutaneous injection and USDA-IBDV challenge was by eye drop at day 29 posthatch.

Data from this experiment are given in part in table 19. Our results show that, at a dose of 338 units of VNF and at a vaccine dose of 0.01x (2.24 $EID_{50}$/dose), bursas were protected from the vaccine virus at days 15 and 22, and were solidly immune to USDA challenge strain at day 29. After USDA challenge on day 29 there was normal body weight gain and no mortality in this group.

TABLE 19

Day 1 Posthatch Dose Titration Vaccination in SPF Chickens Using SANOFI IBD-BLEN Plus Viral Neutralization Factor (VNF) and Evaluation of Bursal Parameters and IBDV Antibody Titers at Day 15, Day 22, and 4 Days post USDA-IBDV Challenge[1] Given on Day 29[2] (Example 15)

| Group Number | Isolator Number | IBDV-BLEN Dose[3] | VNF Units[4] | Bursa Weight (gm) | | | Relative Bursa Weight (g/kg) | | | IBDV Antibody Titer (ELISA) | | |
|---|---|---|---|---|---|---|---|---|---|---|---|---|
| | | | | Day 15 | Day 22 | Day 33 | Day 15 | Day 22 | Day 33 | Day 15 | Day 22 | Day 33 |
| 1 | 6 | Negative | | .203* | .317* | .763* | 1.54 | 1.54 | 2.04 | 366 | 917 | 2711 |
| 1 | 17 | Control | | .622 | 1.229 | 2.145 | 4.72 | 5.86 | 5.95 | 10 | 55 | 4 |
| 2 | 20 | Positive | | .600 | 1.151 | 1.064 | 4.57 | 5.83 | 4.02 | 9 | 104 | 52 |
| 2 | 16 | Control | | .710 | 1.222 | 1.576 | 5.18 | 5.91 | 5.55 | 57 | 67 | 46 |
| 3 | 9 | .01x | | .222 | .362 | .890 | 1.67 | 1.80 | 2.27 | 722 | 824 | 1720 |
| 3 | 2 | | | .189 | .401 | .863 | 1.38 | 1.86 | 2.40 | 1055 | 1794 | 2480 |
| 4 | 1 | .01x | 338 | .632 | .397* | .482* | 4.76 | 2.12 | 1.30 | 50 | 696 | 1645 |
| 4 | 3 | | | .637 | 1.233 | .559 | 4.78 | 6.03 | 1.60 | 16 | 39 | 1677 |
| 5 | 15 | .01x | 34 | .641 | 1.166 | 1.866 | 4.74 | 5.78 | 5.71 | 27 | 11 | 38 |
| 5 | 19 | | | .552 | 1.081 | 1.436 | 4.27 | 5.66 | 5.06 | 120 | 3 | 63 |
| 6 | 8 | .001x | | .194 | .423 | 1.177 | 1.48 | 2.03 | 3.04 | 1201 | 1072 | 2037 |
| 6 | 12 | | | .181 | .376 | .708 | 1.42 | 1.83 | 2.07 | 499 | 1182 | 1539 |
| 7 | 13 | .001x | 338 | .661 | 1.340 | 1.824 | 4.74 | 6.54 | 5.45 | 40 | 34 | 74 |
| 7 | 18 | | | .706 | 1.120 | 1.626 | 5.46 | 5.37 | 5.4 | 76 | 71 | 34 |
| 8 | 5 | .001x | 34 | .707 | 1.122 | 1.492 | 5.06 | 5.74 | 4.48 | 17 | 168 | 26 |
| 8 | 11 | | | .638 | 1.480 | 1.630 | 4.57 | 6.41 | 4.89 | 114 | 41 | 37 |
| 9 | 10 | VNF alone | 338 | .604 | 1.222 | 1.752 | 4.60 | 6.38 | 4.96 | 50 | 130 | 72 |
| 9 | 14 | 1:3 | | .624 | .983* | .440* | 4.39 | 5.30 | 1.31 | 58 | 39 | 1163 |
| 10 | 7 | VNF alone | 34 | .190* | .225* | 0.449* | 1.61 | 1.32 | 1.26 | 573 | 750 | 2636 |
| 10 | 4 | 1:30 | | .748 | 1.252 | 2.080 | 5.16 | 5.95 | 6.18 | 60 | 3 | 163 |
| 11 | 12 | .0001x | 3.4 | .682 | 1.094 | 1.507 | 5.11 | 5.54 | 5.18 | 86 | 6 | 28 |

[1]USDA-IBDV Challenge strain administered by eye-drop at Day 29 posthatch at 47 $EID_{50}$/bird to every group except negative control.
[2]Statistical analysis not shown.
[3]A 0.01X dose of SANOFI IBD-BLEN contained 2.24 $EID_{50}$/dose (Lot #29967).
[4]Viral neutralizing activity is expressed as units/50 μl dose, whole serum containing VNF from SC Hyline chickens.
*Groups that were contaminated with IBDV.

The foregoing examples are illustrative of the present invention, and are not to be taken as limiting thereof. The invention is defined by the following claims, with equivalents of the claims to be included therein.

That which is claimed is:

1. A method of producing active immunity against Infectious Bursal Disease in an avian subject, said method comprising:
   administering to the subject a formulation consisting essentially of a vaccine complex comprising live Infectious Bursal Disease Virus and a neutralizing factor bound to the live virus;
   said live virus being a pathogenic virus capable of causing disease in said subject;
   said neutralizing factor selected from the group consisting of antibodies and antibody fragments which neutralize live virus;
   said vaccine complex administered in an amount effective to produce an active immune response to the live virus in the subject.

2. A method according to claim 1, wherein the neutralizing factor is selected from the group consisting of IgG immunoglobulins and IgG immunoglobulin fragments.

3. A method according to claim 1, wherein the neutralizing factor is of polyclonal origin.

4. A method according to claim 1, wherein the subject is administered the vaccine complex subcutaneously.

5. A method according to claim 1, wherein the subject is administered the vaccine complex by intraperitoneal injection.

6. A method according to claim 1, wherein the subject is administered the vaccine complex by intramuscular injection.

7. A method according to claim 1, wherein the subject is a bird and said administering step is carried out in ovo.

8. A method according to claim 1, wherein the subject has not previously been infected by the live virus.

9. A vaccine preparation useful for producing active immunity against Infectious Bursal Disease in an avian subject, said vaccine preparation comprising:
   a pharmaceutically acceptable formulation consisting essentially of a vaccine complex;
   said vaccine complex further comprising a live Infectious Bursal Disease Virus and a neutralizing factor bound to said live virus;
   said live virus being a pathogenic virus capable of causing disease in said subject;
   said neutralizing factor selected from the group consisting of antibodies and antibody fragments which neutralizing the live virus;
   said vaccine complex included in said pharmaceutically acceptable formulation in an amount effective to produce an active immune response to said live virus in said subject.

10. A vaccine preparation as claimed in claim 9, wherein said pharmaceutically acceptable formulation is lyophylized.

11. A vaccine preparation as claimed in claim 9, wherein said pharmaceutically acceptable formulation comprises a pharmaceutically acceptable carrier.

12. A vaccine preparation as claimed in claim 11, wherein said pharmaceutically acceptable carrier is a liquid carrier.

13. A vaccine preparation as claimed in claim 11, wherein said pharmaceutically acceptable carrier is an aqueous carrier.

14. A vaccine preparation as claimed in claim 9, said pharmaceutically acceptable formulation further comprising an adjuvant.

15. A vaccine preparation as claimed in claim 9, said pharmaceutically acceptable formulation further comprising a stabilizer.

16. A vaccine preparation as claimed in claim 9, wherein said neutralizing factor is selected from the group consisting of IgG immunoglobulins and IgG immunoglobulin fragments.

17. A vaccine preparation as claimed in claim 9, wherein said neutralizing factor is a polyclonal factor.

18. An article of manufacture comprising a closed, pathogen-impermeable container and a sterile vaccine preparation enclosed within said container, said vaccine preparation useful for producing active immunity against Infectious Bursal Disease in an avian subject, said vaccine preparation comprising:
a pharmaceutically acceptable formulation consisting essentially of a vaccine complex;
said vaccine complex comprising a live Infectious Bursal Disease Virus and a neutralizing factor bound to said live virus;
said live virus being a pathogenic virus capable of causing disease in said subject;
said neutralizing factor selected from the group consisting of antibodies and antibody fragments which neutralize said live virus;
said vaccine complex included in said pharmaceutically acceptable carried in an amount effective to produce an active immune response to said live virus in said subject.

19. An article of manufacture as claimed in claim 18, wherein said pharmaceutically acceptable formulation is lyophylized.

20. An article of manufacture as claimed in claim 18, wherein said pharmaceutically acceptable formulation comprises a pharmaceutically acceptable carrier.

21. An article of manufacture as claimed in claim 20, wherein said pharmaceutically acceptable carrier is a liquid carrier.

22. An article of manufacture as claimed in claim 20, wherein said pharmaceutically acceptable carrier is an aqueous carrier.

23. An article of manufacture as claimed in claim 18, said pharmaceutically acceptable formulation further comprising an adjuvant.

24. An article of manufacture as claimed in claim 18, said pharmaceutically acceptable formulation further comprising a stabilizer.

25. An article of manufacture as claimed in claim 18, wherein said neutralizing factor is selected from the group consisting of IgG immunoglobulins and IgG immunoglobulin fragments.

26. An article of manufacture as claimed in claim 18, wherein said neutralizing factor is a polyclonal factor.

27. A method of producing active immunity against Infectious Bursal Disease in an avian subject, said method comprising:
administering to the subject a vaccine complex further comprising live Infectious Bursal Disease Virus and a neutralizing factor bound to the live virus;
the neutralizing factor selected from the group consisting of antibodies and antibody fragments which neutralize the live virus;
said live virus being a pathogenic virus capable of causing disease in said subject;
and wherein the neutralizing factor is of monoclonal origin;
said vaccine complex administered in an amount effective to produce an active immune response to the live virus in the subject.

28. A method according to claim 27, wherein the neutralizing factor is selected from the group consisting of IgG immunoglobulins and IgG immunoglobulin fragments.

29. A method according to claim 27, wherein the subject is administered the vaccine complex subcutaneously.

30. A method according to claim 27, wherein the subject is administered the vaccine complex by intraperitoneal injection.

31. A method according to claim 27, wherein the subject is administered the vaccine complex by intramuscular injection.

32. A method according to claim 27, wherein the subject is a bird and said administering step is carried out in ovo.

33. A method according to claim 27, wherein the subject has not previously been infected by the live virus.

34. A vaccine preparation useful for producing active immunity against Infectious Bursal Disease in an avian subject, said vaccine preparation comprising:
a pharmaceutically acceptable formulation comprising a vaccine complex;
said vaccine complex further comprising live Infectious Bursal Disease Virus and a neutralizing factor bound to said live virus;
said live virus being a pathogenic virus capable of causing disease in said subject;
said neutralizing factor selected from the group consisting of antibodies and antibody fragments which neutralize the live virus;
and wherein said neutralizing factor is a monoclonal factor;
said vaccine complex included in said pharmaceutically acceptable formulation in an amount effective to produce and active immune response to said live virus in said subject.

35. A vaccine preparation as claimed in claim 34, wherein said pharmaceutically acceptable formulation is lyophylized.

36. A vaccine preparation as claimed in claim 34, wherein said pharmaceutically acceptable formulation comprises a pharmaceutically acceptable carrier.

37. A vaccine preparation as claimed in claim 36, wherein said pharmaceutically acceptable carrier is a liquid carrier.

38. A vaccine preparation as claimed in claim 36, wherein said pharmaceutically acceptable carrier is an aqueous carrier.

39. A vaccine preparation as claimed in claim 34, said pharmaceutically acceptable formulation further comprising an adjuvant.

40. A vaccine preparation as claimed in claim 34, said pharmaceutically acceptable formulation further comprising a stabilizer.

41. A vaccine preparation as claimed in claim 34, wherein said neutralizing factor is selected from the group consisting of IgG immunoglobulins and IgG immunoglobulin fragments.

42. An article of manufacture comprising a closed, pathogen-impermeable container and a sterile vaccine preparation enclosed within said container, said vaccine preparation useful for producing active immunity against Infectious Bursal Disease in an avian subject, said vaccine preparation comprising:
- a pharmaceutically acceptable formulation comprising a vaccine complex;
- said vaccine complex further comprising live Infectious Bursal Disease Virus and a neutralizing factor bound to said live virus, said live virus being a pathogenic virus capable of causing disease in said subject;

said neutralizing factor selected from the group consisting of antibodies and antibody fragments which neutralize the live virus;

and wherein said neutralizing factor is a monoclonal factor;

said vaccine complex included in said pharmaceutically acceptable carrier in an amount effective to produce an active immune response to said live virus in said subject.

43. An article of manufacture as claimed in claim 41, wherein said pharmaceutically acceptable formulation is lyophilized.

44. An article of manufacture as claimed in claim 42, wherein said pharmaceutically acceptable formulation includes a pharmaceutically acceptable carrier.

45. An article of manufacture as claimed in claim 44, wherein said pharmaceutically acceptable carrier is a liquid carrier.

46. An article of manufacture as claimed in claim 44, wherein said pharmaceutically acceptable carrier is an aqueous carrier.

47. An article of manufacture as claimed in claim 42, said pharmaceutically acceptable formulation further comprising an adjuvant.

48. An article of manufacture as claimed in claim 42, said pharmaceutically acceptable formulation further comprising a stabilizer.

49. An article of manufacture as claimed in claim 42, wherein said neutralizing factor is selected from the group consisting of IgG immunoglobulins and IgG immunoglobulin fragments.

* * * * *

UNITED STATES PATENT AND TRADEMARK OFFICE
CERTIFICATE OF CORRECTION

PATENT NO. : 5,397,569

DATED : March 14, 1995

INVENTOR(S) : Craig E. Whitfill, John A. Thomas, Tommy L Fredericksen, Julius K. Tyczkowski and J. Paul Thaxton, Jr.

It is certified that error appears in the above-indentified patent and that said Letters Patent is hereby corrected as shown below:

Column 15, Table 7, delete "ml$^4$" and insert --ml--.

Column 16, Table 7, delete "ml$^4$" and insert --ml--.

Column 25, Table 18, delete "1 0.01X" and insert --A 0.01X--.

Column 32, line 7, delete "41," and insert --42,--.

Signed and Sealed this

Sixth Day of May, 1997

*Attest:*

*Attesting Officer*

BRUCE LEHMAN

*Commissioner of Patents and Trademarks*